United States Patent
Clausen

(10) Patent No.: US 11,707,365 B2
(45) Date of Patent: *Jul. 25, 2023

(54) MAGNETIC LOCKING MECHANISM FOR PROSTHETIC OR ORTHOTIC JOINTS

(71) Applicant: Össur Iceland ehf, Reykjavik (IS)

(72) Inventor: Arinbjörn Viggo Clausen, Reykjavik (IS)

(73) Assignee: Össur Iceland ehf, Reykjavik (IS)

( * ) Notice: Subject to any disclaimer, the term of this patent is extended or adjusted under 35 U.S.C. 154(b) by 503 days.

This patent is subject to a terminal disclaimer.

(21) Appl. No.: 16/901,995

(22) Filed: Jun. 15, 2020

(65) Prior Publication Data
US 2020/0375764 A1    Dec. 3, 2020

Related U.S. Application Data

(63) Continuation of application No. 15/923,625, filed on Mar. 16, 2018, now Pat. No. 10,722,386, which is a
(Continued)

(51) Int. Cl.
*A61F 2/66* (2006.01)
*A61F 2/68* (2006.01)
(Continued)

(52) U.S. Cl.
CPC ............ *A61F 2/66* (2013.01); *A61F 2/6607* (2013.01); *A61F 2/76* (2013.01); *G05G 7/00* (2013.01);
(Continued)

(58) Field of Classification Search
CPC .. A61F 2/60; A61F 2/66; A61F 2/6607; A61F 2/38; A61F 2/76; A61F 2002/5016;
(Continued)

(56) References Cited

U.S. PATENT DOCUMENTS

| 1,951,622 A | 3/1934 | McElroy |
| 2,475,373 A | 7/1949 | Catranis |

(Continued)

FOREIGN PATENT DOCUMENTS

| CN | 1074109 | 7/1993 |
| CN | 1376856 | 10/2002 |

(Continued)

OTHER PUBLICATIONS

Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.

(Continued)

*Primary Examiner* — Marcia L Watkins
(74) *Attorney, Agent, or Firm* — Knobbe, Martens, Olson & Bear, LLP

(57) ABSTRACT

A magnetic locking actuator for a prosthetic or orthotic device is provided. The actuator includes a first component including one or more magnets and a second component including one or more magnets. The first and second components are coupled to separate portions of the device. The magnets allow for adjustment of a length of the actuator to adjust an angular orientation of the first and second portions of the device. When magnets in the second component are aligned with magnets in the first component having an opposite polarity, a position of the second component is fixed relative to the first component, locking the actuator. When magnets in the second component are not aligned with magnets in the first component having the opposite polarity, the position of the second component is adjustable relative to the first component, thereby allowing adjustment of the height of the actuator.

21 Claims, 28 Drawing Sheets

Related U.S. Application Data continuation of application No. 15/268,340, filed on Sep. 16, 2016, now Pat. No. 9,949,850.

(60) Provisional application No. 62/220,823, filed on Sep. 18, 2015.

(51) Int. Cl.
  *A61F 2/76* (2006.01)
  *G05G 7/00* (2006.01)
  *A61F 2/50* (2006.01)
  *G05G 7/12* (2006.01)

(52) U.S. Cl.
  CPC . *A61F 2002/502* (2013.01); *A61F 2002/5084* (2013.01); *A61F 2002/6614* (2013.01); *A61F 2002/6863* (2013.01); *G05G 7/12* (2013.01)

(58) Field of Classification Search
  CPC ........ A61F 2002/502; A61F 2002/5084; A61F 2002/6854; A61F 2002/6863
  See application file for complete search history.

(56) References Cited

U.S. PATENT DOCUMENTS

| | | |
|---|---|---|
| 2,568,051 A | 9/1951 | Catranis |
| 2,660,029 A | 11/1953 | Geyer |
| 2,930,659 A | 3/1960 | Willmore |
| 3,022,400 A | 2/1962 | Ahlefeldt |
| 3,229,545 A | 1/1966 | Hautau |
| 3,579,276 A | 5/1971 | Newell |
| 3,678,311 A | 7/1972 | Mattingly |
| 3,803,926 A | 4/1974 | Winter |
| 3,820,168 A | 6/1974 | Horvath |
| 3,995,324 A | 12/1976 | Burch |
| 4,030,141 A | 6/1977 | Graupe |
| 4,065,815 A | 1/1978 | Sen-Jung |
| 4,152,787 A | 5/1979 | Meggyesy |
| 4,179,759 A | 12/1979 | Smith |
| 4,209,860 A | 7/1980 | Graupe |
| 4,212,087 A | 7/1980 | Mortensen |
| 4,387,472 A | 6/1983 | Wilson |
| 4,398,109 A | 8/1983 | Kuwako et al. |
| 4,420,714 A | 12/1983 | Petersen et al. |
| 4,501,981 A | 2/1985 | Hansen |
| 4,521,924 A | 6/1985 | Jacobsen et al. |
| 4,558,704 A | 12/1985 | Petrofsky |
| 4,569,352 A | 2/1986 | Petrofsky et al. |
| 4,652,266 A | 3/1987 | Truesdell |
| 4,711,242 A | 12/1987 | Petrofsky |
| 4,776,852 A | 10/1988 | Ruble |
| 4,876,944 A | 10/1989 | Wilson et al. |
| 4,892,554 A | 1/1990 | Robinson |
| 4,944,755 A | 7/1990 | Hennequin et al. |
| 4,994,086 A | 2/1991 | Edwards |
| 5,044,360 A | 9/1991 | Janke |
| 5,062,856 A | 11/1991 | Sawamura et al. |
| 5,062,857 A | 11/1991 | Berringer |
| 5,092,902 A | 3/1992 | Adams et al. |
| 5,112,296 A | 5/1992 | Beard et al. |
| 5,112,356 A | 5/1992 | Harris et al. |
| 5,139,525 A | 8/1992 | Kristinsson |
| 5,153,496 A | 10/1992 | LaForge |
| 5,181,931 A | 1/1993 | Van de Veen |
| 5,201,772 A | 4/1993 | Maxwell |
| 5,217,500 A | 6/1993 | Phillips |
| 5,219,365 A | 6/1993 | Sabolich |
| 5,252,102 A | 10/1993 | Singer et al. |
| 5,336,269 A | 8/1994 | Smits |
| 5,376,133 A | 12/1994 | Gramnaes |
| 5,376,137 A | 12/1994 | Shorter et al. |
| 5,376,141 A | 12/1994 | Phillips |
| 5,383,939 A | 1/1995 | James |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,443,521 A | 8/1995 | Knoth et al. |
| 5,443,524 A | 8/1995 | Sawamura et al. |
| 5,443,528 A | 8/1995 | Allen |
| 5,466,083 A | 11/1995 | Hogg |
| 5,472,412 A | 12/1995 | Knoth |
| 5,476,441 A | 12/1995 | Durfee et al. |
| 5,504,415 A | 4/1996 | Podrazhansky et al. |
| 5,545,232 A | 8/1996 | Van de Veen |
| 5,545,233 A | 8/1996 | Fitzlaff |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,586,557 A | 12/1996 | Nelson et al. |
| 5,611,508 A | 3/1997 | Palmero |
| 5,650,704 A | 7/1997 | Pratt et al. |
| 5,656,915 A | 8/1997 | Eaves |
| 5,660,495 A | 8/1997 | Ukawa |
| 5,662,693 A | 9/1997 | Johnson et al. |
| 5,704,945 A | 1/1998 | Wagner et al. |
| 5,704,946 A | 1/1998 | Greene |
| 5,728,170 A | 3/1998 | Becker et al. |
| 5,746,774 A | 5/1998 | Kramer |
| 5,751,083 A | 5/1998 | Tamura et al. |
| 5,779,735 A | 7/1998 | Molino |
| 5,800,568 A | 9/1998 | Atkinson et al. |
| 5,888,212 A | 3/1999 | Petrofsky et al. |
| 5,888,213 A | 3/1999 | Sears et al. |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,913,401 A * | 6/1999 | Tamura ................. H02K 49/102 198/619 |
| 5,919,149 A | 7/1999 | Allum |
| 5,955,667 A | 9/1999 | Fyfe |
| 5,957,981 A | 9/1999 | Gramnaes |
| 5,972,035 A | 10/1999 | Blatchford |
| 5,982,156 A | 11/1999 | Weimer et al. |
| 5,998,930 A | 12/1999 | Upadhyay et al. |
| 6,007,582 A | 12/1999 | May |
| 6,061,577 A | 5/2000 | Andrieu et al. |
| 6,084,326 A * | 7/2000 | Nagai ....................... H02K 7/06 74/424.89 |
| 6,091,977 A | 7/2000 | Tarjan et al. |
| 6,113,642 A | 9/2000 | Petrofsky et al. |
| 6,129,766 A | 10/2000 | Johnson et al. |
| 6,164,967 A | 12/2000 | Sale |
| 6,165,226 A | 12/2000 | Wagner |
| 6,183,425 B1 | 2/2001 | Whalen et al. |
| 6,187,051 B1 | 2/2001 | Gerad van de Veen |
| 6,195,921 B1 | 3/2001 | Truong |
| 6,206,932 B1 | 3/2001 | Johnson |
| 6,206,933 B1 | 3/2001 | Shorter et al. |
| 6,241,775 B1 | 6/2001 | Blatchford |
| 6,301,964 B1 | 10/2001 | Fyfe et al. |
| 6,350,286 B1 | 2/2002 | Atkinson et al. |
| 6,361,570 B1 | 3/2002 | Gow |
| 6,373,152 B1 | 4/2002 | Wang et al. |
| 6,409,695 B1 | 6/2002 | Connelly |
| 6,423,098 B1 | 7/2002 | Biedermann |
| 6,425,925 B1 | 7/2002 | Grundei |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,537,322 B1 | 3/2003 | Johnson et al. |
| 6,587,728 B2 | 7/2003 | Fang et al. |

(56) References Cited

U.S. PATENT DOCUMENTS

| | | | |
|---|---|---|---|
| 6,602,295 B1 | 8/2003 | Doddroe et al. | |
| 6,610,101 B2 | 8/2003 | Herr et al. | |
| 6,662,672 B2* | 12/2003 | Someya | F16H 25/20 74/89.4 |
| 6,663,673 B2 | 12/2003 | Christensen | |
| 6,671,531 B2 | 12/2003 | Al-Ali et al. | |
| 6,679,920 B2 | 1/2004 | Biedermann et al. | |
| 6,695,885 B2 | 2/2004 | Schulman et al. | |
| 6,719,806 B1 | 4/2004 | Zahedi et al. | |
| 6,740,123 B2 | 5/2004 | Davalli et al. | |
| 6,743,260 B2 | 6/2004 | Townsend et al. | |
| 6,755,870 B1 | 6/2004 | Biedermann et al. | |
| 6,761,743 B1 | 7/2004 | Johnson | |
| 6,764,520 B2 | 7/2004 | Deffenbaugh et al. | |
| 6,767,370 B1 | 7/2004 | Mosier et al. | |
| 6,770,045 B2 | 8/2004 | Naft et al. | |
| 6,875,241 B2 | 4/2005 | Christensen | |
| 6,876,135 B2 | 4/2005 | Pelrine et al. | |
| 6,908,488 B2 | 6/2005 | Paasivaara et al. | |
| 6,918,308 B2 | 7/2005 | Biedermann | |
| 6,955,692 B2 | 10/2005 | Grundei | |
| 6,966,933 B2 | 11/2005 | Christensen | |
| 7,025,792 B2 | 4/2006 | Collier | |
| 7,029,500 B2 | 4/2006 | Martin | |
| 7,063,727 B2 | 6/2006 | Phillips et al. | |
| 7,091,679 B2 | 8/2006 | Schroeder et al. | |
| 7,118,601 B2 | 10/2006 | Yasui | |
| 7,131,998 B2 | 11/2006 | Pasolini | |
| 7,137,998 B2 | 11/2006 | Bédard et al. | |
| 7,147,667 B2 | 12/2006 | Bédard et al. | |
| 7,164,967 B2 | 1/2007 | Etienne-Cummings et al. | |
| 7,190,096 B2 | 3/2007 | Blanding et al. | |
| 7,308,333 B2 | 12/2007 | Kern et al. | |
| 7,313,463 B2 | 12/2007 | Herr et al. | |
| 7,314,490 B2 | 1/2008 | Bédard et al. | |
| 7,462,201 B2 | 12/2008 | Christensen | |
| 7,503,900 B2 | 3/2009 | Goswami | |
| 7,520,904 B2 | 4/2009 | Christensen | |
| 7,531,006 B2 | 5/2009 | Clausen et al. | |
| 7,637,957 B2 | 12/2009 | Ragnarsdottir et al. | |
| 7,637,959 B2 | 12/2009 | Clausen et al. | |
| 7,655,050 B2 | 2/2010 | Palmer et al. | |
| 7,736,394 B2 | 6/2010 | Bedard et al. | |
| 7,811,334 B2 | 10/2010 | Ragnarsdottir et al. | |
| 7,867,284 B2 | 1/2011 | Bédard et al. | |
| 7,888,846 B2 | 2/2011 | Ohtera et al. | |
| 7,898,121 B2 | 3/2011 | Ramsay et al. | |
| 7,918,808 B2 | 4/2011 | Simmons | |
| 7,949,429 B2 | 5/2011 | Ohtera et al. | |
| 8,048,172 B2 | 11/2011 | Jonsson et al. | |
| 8,057,550 B2 | 11/2011 | Clausen | |
| 8,075,633 B2 | 12/2011 | Herr et al. | |
| 8,083,807 B2 | 12/2011 | Auberger et al. | |
| 8,092,550 B2* | 1/2012 | McCarvill | A61F 2/76 623/55 |
| 8,109,890 B2 | 2/2012 | Kamiar et al. | |
| 8,231,687 B2 | 7/2012 | Bédard et al. | |
| 7,431,737 C1 | 12/2013 | Ragnarsdottir et al. | |
| 8,657,886 B2 | 2/2014 | Clausen et al. | |
| 8,709,097 B2 | 4/2014 | Jonsson et al. | |
| 7,896,927 C1 | 5/2014 | Clausen et al. | |
| 9,017,419 B1 | 4/2015 | Landry et al. | |
| 9,114,029 B2 | 8/2015 | Ásgeirsson et al. | |
| 9,271,851 B2 | 3/2016 | Claussen et al. | |
| 9,351,854 B2 | 5/2016 | Jónsson et al. | |
| 9,949,850 B2 | 4/2018 | Clausen | |
| 10,722,386 B2* | 7/2020 | Clausen | A61F 2/66 |
| 2002/0043880 A1 | 4/2002 | Suzuki et al. | |
| 2002/0087213 A1 | 7/2002 | Bertram | |
| 2002/0087216 A1 | 7/2002 | Atkinson et al. | |
| 2003/0120354 A1 | 6/2003 | Doddroe et al. | |
| 2003/0163203 A1 | 8/2003 | Nycz et al. | |
| 2003/0163206 A1 | 8/2003 | Yasui | |
| 2004/0064195 A1 | 4/2004 | Herr | |
| 2005/0071017 A1 | 3/2005 | Lecomte et al. | |
| 2005/0107889 A1 | 5/2005 | Bédard et al. | |
| 2005/0137717 A1 | 6/2005 | Gramnaes | |
| 2005/0192677 A1 | 9/2005 | Ragnarsdottir et al. | |
| 2005/0283257 A1 | 12/2005 | Bisbee et al. | |
| 2006/0122710 A1 | 6/2006 | Bédard et al. | |
| 2006/0136072 A1 | 6/2006 | Bisbee et al. | |
| 2006/0249315 A1 | 11/2006 | Herr et al. | |
| 2007/0027557 A1 | 2/2007 | Jonsson et al. | |
| 2007/0043449 A1 | 2/2007 | Herr et al. | |
| 2007/0050047 A1 | 3/2007 | Ragnarsdottir et al. | |
| 2007/0061016 A1 | 3/2007 | Kuo et al. | |
| 2007/0123997 A1 | 5/2007 | Herr et al. | |
| 2007/0162152 A1 | 7/2007 | Herr et al. | |
| 2008/0004718 A1 | 1/2008 | Mosler | |
| 2008/0122303 A1 | 5/2008 | Santo et al. | |
| 2008/0306612 A1 | 12/2008 | Mosier | |
| 2009/0204230 A1 | 8/2009 | Kaltenborn et al. | |
| 2010/0030343 A1 | 2/2010 | Hansen et al. | |
| 2010/0042228 A1 | 2/2010 | Doddroe et al. | |
| 2010/0094431 A1 | 4/2010 | Albrecht-Laatsch | |
| 2010/0114329 A1 | 5/2010 | Casler et al. | |
| 2010/0131101 A1 | 5/2010 | Engeberg et al. | |
| 2010/0179668 A1 | 7/2010 | Herr et al. | |
| 2011/0015761 A1 | 1/2011 | Celebi et al. | |
| 2011/0082566 A1 | 4/2011 | Herr et al. | |
| 2011/0106274 A1 | 5/2011 | Ragnarsdottir et al. | |
| 2012/0130508 A1 | 5/2012 | Harris et al. | |
| 2012/0209405 A1 | 8/2012 | Herr et al. | |
| 2012/0283845 A1 | 11/2012 | Herr et al. | |
| 2013/0218298 A1 | 8/2013 | Mosler | |
| 2014/0039642 A1 | 2/2014 | Nijiman et al. | |
| 2014/0243997 A1 | 8/2014 | Clausen et al. | |
| 2015/0066153 A1 | 3/2015 | Palmer, III et al. | |
| 2015/0164661 A1 | 6/2015 | Ragnarsdottir et al. | |
| 2015/0328020 A1 | 11/2015 | Clausen et al. | |
| 2016/0367384 A1* | 12/2016 | Sigmon | A61F 2/76 |
| 2017/0112640 A1 | 4/2017 | Clausen et al. | |

FOREIGN PATENT DOCUMENTS

| | | |
|---|---|---|
| CN | 2776340 | 5/2006 |
| CN | 1929797 | 3/2007 |
| CN | 101155557 | 4/2008 |
| DE | 42 29 330 | 3/1994 |
| DE | 195 21 464 | 3/1997 |
| EP | 0 549 855 | 7/1993 |
| EP | 0 902 547 | 3/1999 |
| EP | 1 107 420 | 6/2001 |
| EP | 1 166 726 | 1/2002 |
| EP | 1 169 982 | 1/2002 |
| FR | 2 623 086 | 5/1989 |
| GB | 2 201 260 | 8/1988 |
| GB | 2 228 201 | 8/1990 |
| GB | 2 244 006 | 11/1991 |
| GB | 2 260 495 | 4/1993 |
| GB | 2 301 776 | 12/1996 |
| GB | 2 302 949 | 2/1997 |
| GB | 2 338 653 | 12/1999 |
| GB | 2 367 753 | 4/2002 |
| JP | 59-088147 | 5/1984 |
| JP | 59-189843 | 10/1984 |
| JP | 11-000345 | 1/1999 |
| JP | 11-056885 | 3/1999 |
| JP | 2001-277175 | 10/2001 |
| JP | 2002-191654 | 7/2002 |
| JP | 2005-536317 | 12/2005 |
| WO | WO 94/006374 | 3/1994 |
| WO | WO 95/026171 | 10/1995 |
| WO | WO 96/041599 | 12/1996 |
| WO | WO 97/000661 | 1/1997 |
| WO | WO 98/038951 | 9/1998 |
| WO | WO 99/005991 | 2/1999 |
| WO | WO 00/027318 | 5/2000 |
| WO | WO 01/017466 | 3/2001 |
| WO | WO 01/072245 | 10/2001 |
| WO | WO 03/003953 | 1/2003 |
| WO | WO 03/086245 | 10/2003 |
| WO | WO 2004/017871 | 3/2004 |
| WO | WO 2004/017872 | 3/2004 |

(56) References Cited

FOREIGN PATENT DOCUMENTS

| WO | WO 2004/017873 | 3/2004 |
|---|---|---|
| WO | WO 2005/041819 | 5/2005 |
| WO | WO 2005/079712 | 9/2005 |
| WO | WO 2007/027668 | 3/2007 |
| WO | WO 2013/006585 | 1/2013 |
| WO | WO 2014/133975 | 9/2014 |
| WO | WO 2015/157723 | 10/2015 |

OTHER PUBLICATIONS

Blaya, et al., "Adaptive Control of a Variable-Impedance Ankle-Foot Orthosis to Assist Drop-Foot Gait," IEEE Transactions on Neural Systems and Rehabilitation Engineering, vol. 12, No. 1, Mar. 2004, pp. 24-31.

Copes Inc., "Copes/Bionic Ankle," The Most Significant Development in Ankle Prosthetics in Over a Half Century, Brochure, Nov. 1985, pp. 3.

Dietl et al., "Der Einsatz von Elektronik bei Prothesen zur Versorgung der unteren Extremität," Med. Orth. Tech., 1997, vol. 117, pp. 31-35.

Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.

International Search Report and Written Opinion in PCT Application No. PCT/US2016/052339, dated Jan. 5, 2017.

Proteor, "Assembly and Adjustment Instructions for IP50-R," Sep. 2004, pp. 1-21.

Suga et al., "Newly Designed Computer Controlled Knee-Ankle-Foot Orthosis (Intelligent Orthosis)", Prosthetics and Orthotics International, vol. 22, 1998, pp. 230-239.

Townsend et al., "Biomechanics and Modeling of Bipedal Climbing and Descending," Journal of Biomechanics, vol. 9, No. 4, 1976, pp. 227-239.

\* cited by examiner

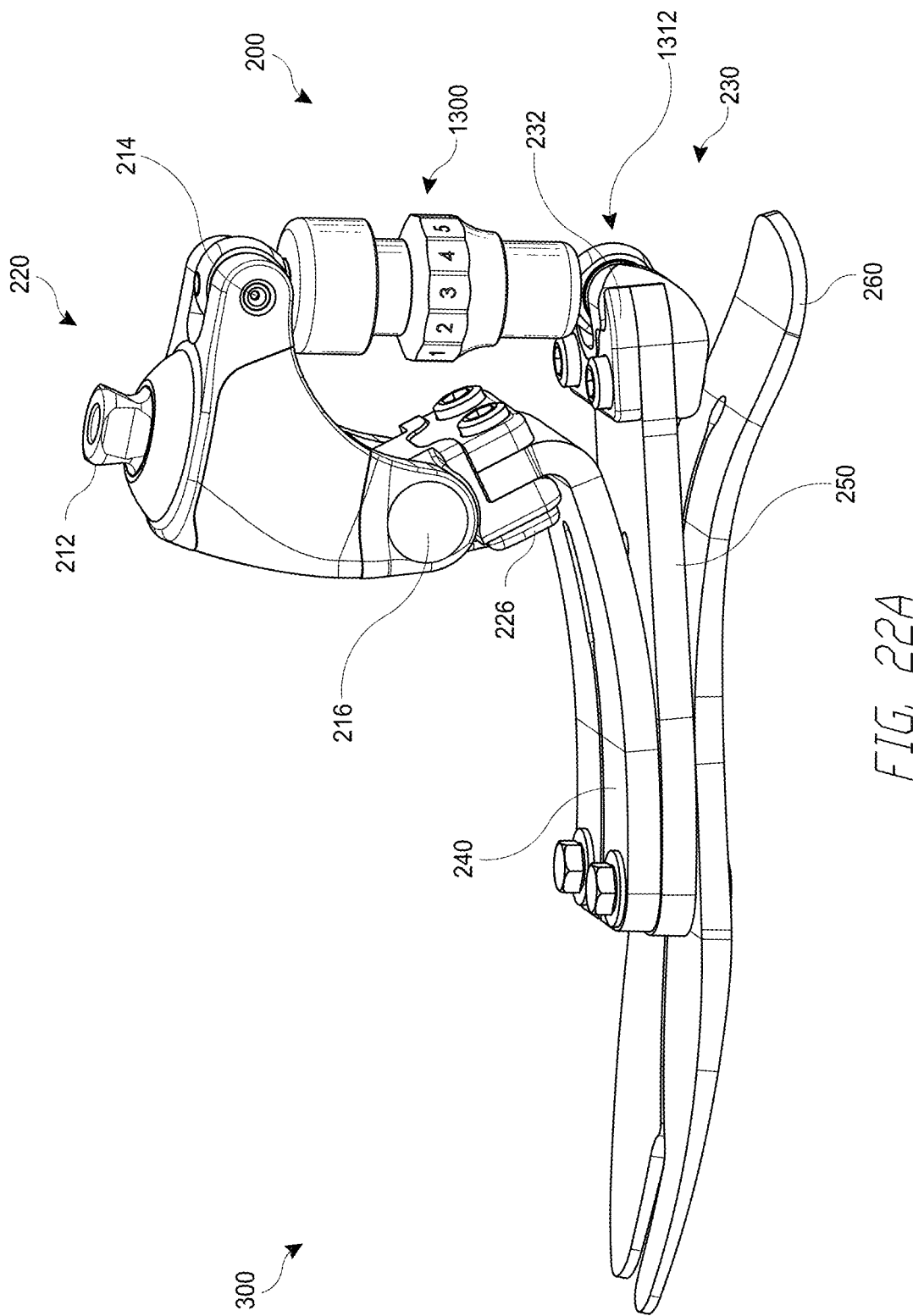

MAGNETIC LOCKING MECHANISM FOR PROSTHETIC OR ORTHOTIC JOINTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. application Ser. No. 15/923,625, filed Mar. 16, 2018, now U.S. Pat. No. 10,722,386, which is a continuation of U.S. application Ser. No. 15/268,340, filed Sep. 16, 2016, now U.S. Pat. No. 9,949,850, issued on Apr. 24, 2018, which claims the priority benefit of U.S. Provisional Application No. 62/220,823, filed Sep. 18, 2015, the entirety of which is incorporated herein by reference.

BACKGROUND

Field

The present application relates to actuators, and more particularly, to actuators used in prosthetic or orthotic joints.

Description of the Related Art

Various types of prosthetic devices are available as artificial substitutes for a missing body part, such as an arm or leg. Prosthetic joints are also available as substitutes for human joints, such as an ankle or knee. Prosthetic joints can include actuators to create motion of the joint, such as to adjust a heel height of the prosthetic foot.

SUMMARY

According to a first aspect of the present disclosure, a prosthetic foot is provided that includes a first plate extending between a proximal end and a distal end, a second plate disposed below the first plate and extending between a proximal end and a distal end, an adapter pivotally coupled to the proximal end of the first plate at a first joint, and a mechanical actuator assembly coupled to the proximal end of the second plate and pivotally coupled to the adapter at a second joint disposed rearward of the first joint, the actuator adjustable to adjust a heel height of the prosthetic foot. The actuator can include a first component having one or more magnets; a second component having one or more magnets, the second component sized to extend into an opening in the first component; wherein when at least one magnet or at least a portion of at least one magnet in the first component having a first polarity is aligned with at least one magnet or at least a portion of at least one magnet in the second component having a second polarity opposite to the first polarity, a position of the second component is substantially fixed relative to the first component, substantially locking the actuator, and wherein when the at least one magnet or at least a portion of at least one magnet in the first component is not aligned with the at least one magnet or at least a portion of at least one magnet in the second component, the position of the second component is adjustable relative to the first component to adjust a heel height of the prosthetic foot.

The prosthetic foot can be arranged such that the magnets are bar magnets.

The prosthetic foot can be arranged such that the first component comprises a connector configured to couple the first component to the adapter and an outer housing, wherein the one or more magnets are disposed in the outer housing and the outer housing is disposed around at least a portion of the connector. The prosthetic foot can be further configured such that the connector comprises a ball joint configured to be coupled to the adapter. The prosthetic foot can be configured such that the connector comprises a threaded shaft configured to engage a first internally threaded portion of the second component. The prosthetic foot can be further configured such that the actuator further comprises a third component comprising a connector configured to couple the actuator to the proximal end of the second plate. The prosthetic foot can be further configured such that the heel height of the prosthetic foot is adjusted by rotating the second component relative to the first and/or third components.

The prosthetic foot can be arranged such that the first and second components define a stepper magnet actuator.

According to another aspect of the present disclosure, an actuator can be provided that includes a first component having one or more magnets; a second component having one or more magnets, the second component sized to extend into an opening in the first component; wherein when at least one magnet or at least a portion of at least one magnet in the first component having a first polarity is aligned with at least one magnet or at least a portion of at least one magnet in the second component having a second polarity opposite to the first polarity, a position of the second component is substantially fixed relative to the first component, substantially locking the actuator, and wherein when the at least one magnet or at least a portion of at least one magnet in the first component is not aligned with the at least one magnet or at least a portion of at least one magnet in the second component, the position of the second component is adjustable relative to the first component to adjust a length of the actuator.

The actuator can be arranged such that the length of the actuator is adjusted by rotating the second component relative to the first component.

The actuator can be arranged such that the actuator is configured for use in a prosthetic or orthotic device.

The actuator can be arranged such that the magnets are bar magnets.

The actuator can be arranged such that the first component comprises a connector configured to couple the first component to a first portion of an orthotic or prosthetic device and an outer housing, wherein the one or more magnets are disposed in the outer housing and the outer housing is disposed around at least a portion of the connector. The actuator can be further arranged such that the connector comprises a ball joint configured to be coupled to the adapter. The actuator can be arranged such that the connector comprises a threaded shaft configured to engage a first internally threaded portion of the second component. The actuator can be further arranged such that the actuator further includes a third component comprising a connector configured to couple the actuator to a second component of the orthotic or prosthetic device. The actuator can be further arranged such that the connector of the third component comprises a threaded shaft configured to engage a second internally threaded portion of the second component. The actuator can be further arranged such that a height of the orthotic or prosthetic device is adjusted by rotating the second component relative to the first and/or third components.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIGS. 22A-22B illustrate the actuator of FIGS. 11-20B incorporated into a prosthetic foot.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below. While the actuator or adjustment mechanism described in the embodiments below is described in the context of a prosthetic joint, one of skill in the art will recognize that the disclosed actuator or adjustment mechanism embodiments can also be implemented in an orthotic or other exoskeleton device, and the scope of the disclosure is intended to cover these as well.

Figure 4:
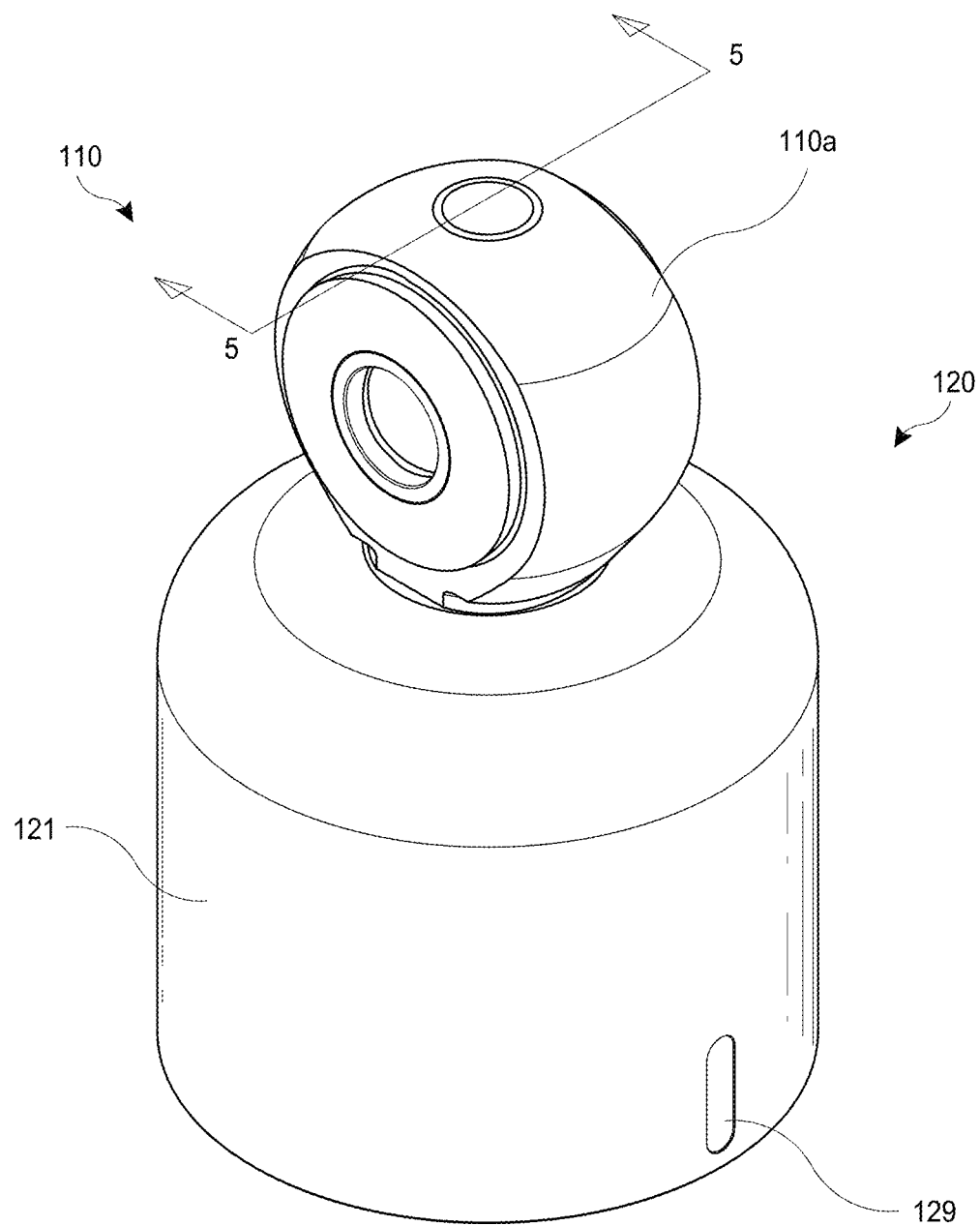
FIG. 4 illustrates an upper component of the actuator of FIGS. 1-3B.
Figure 5:
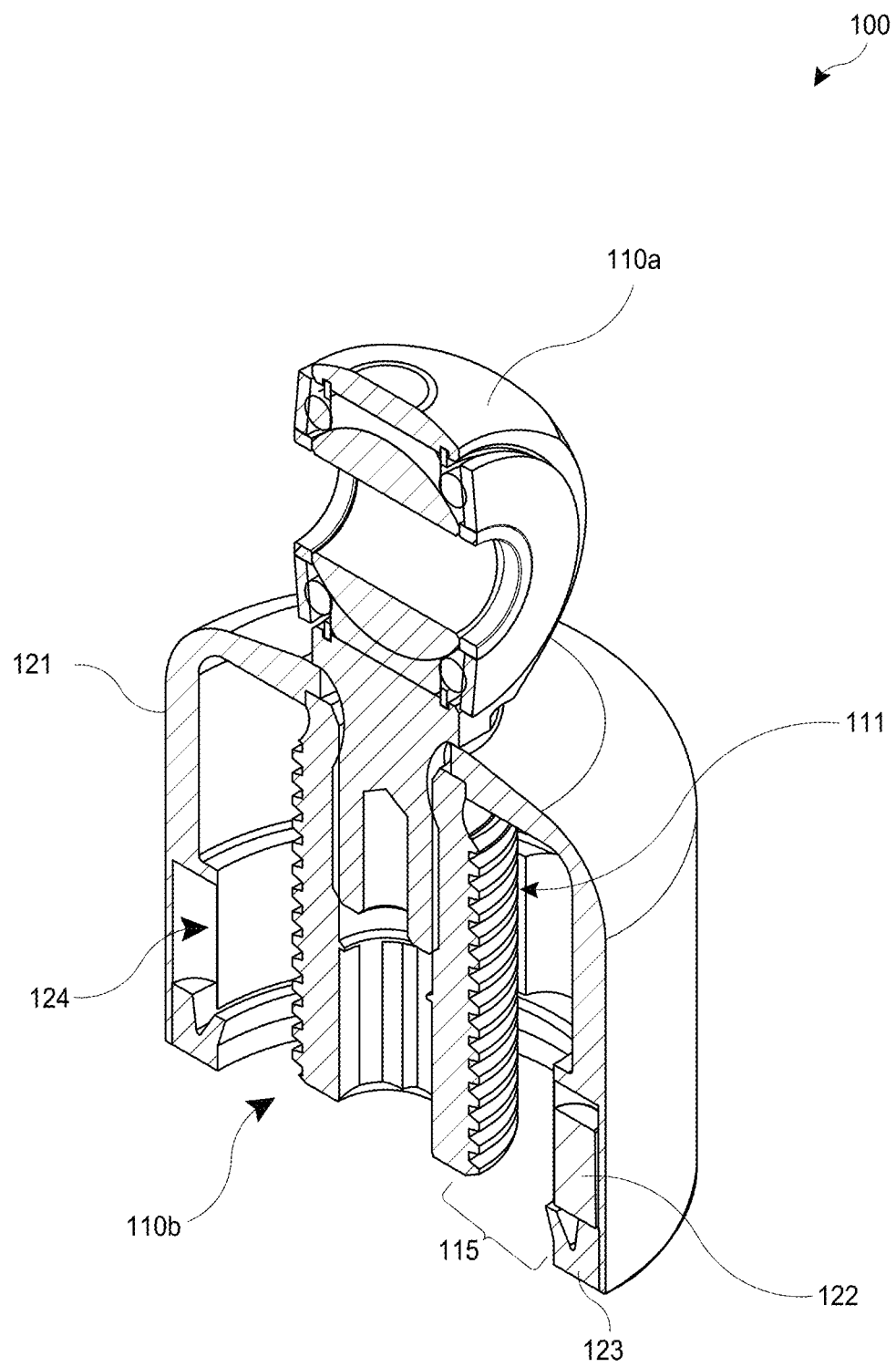
FIG. 5 illustrates a cross-sectional view of the upper component of FIG. 4.
Figure 6:
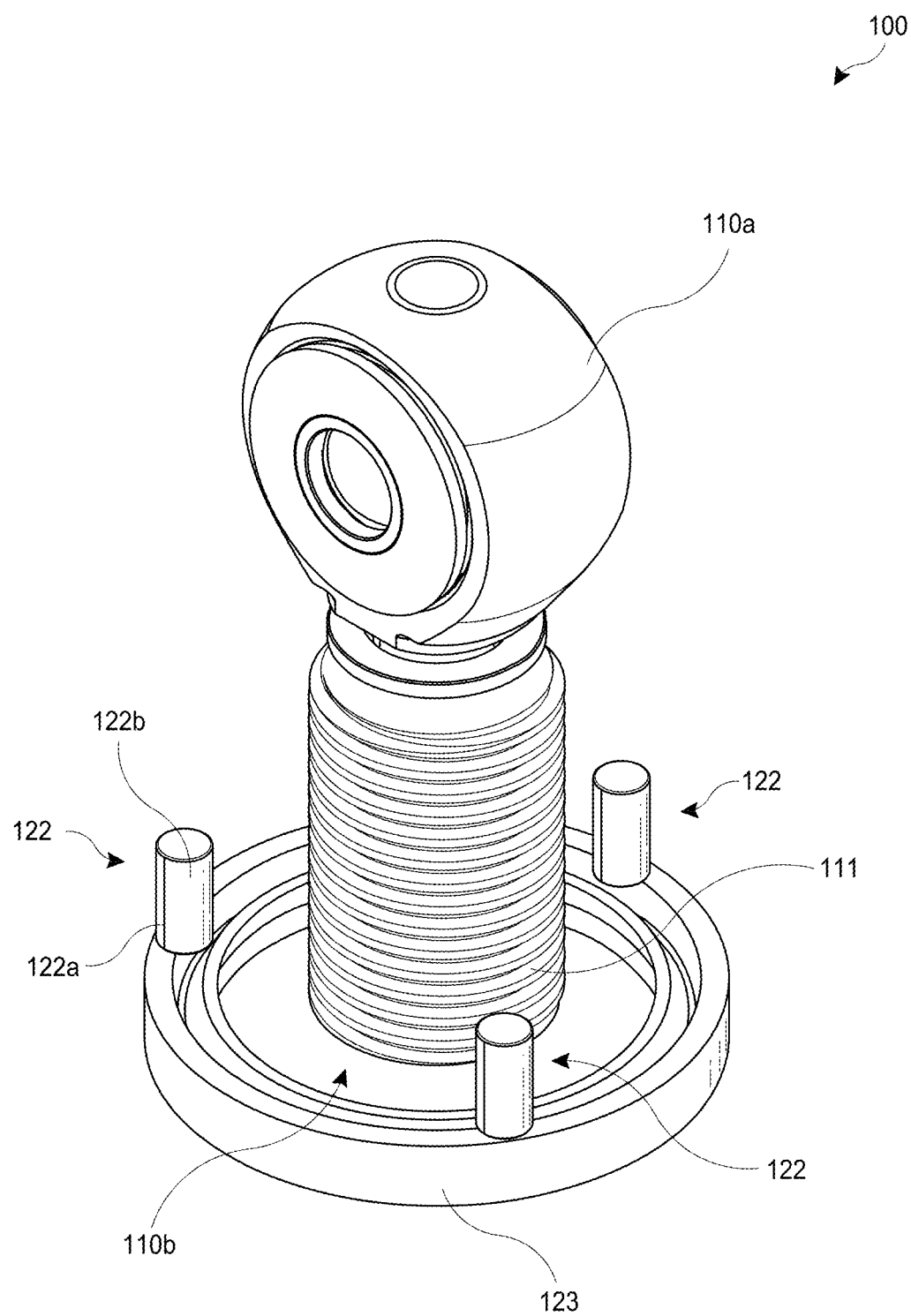
FIG. 6 illustrates the upper component of FIGS. 4-5 with an outer housing removed.
Figure 9:
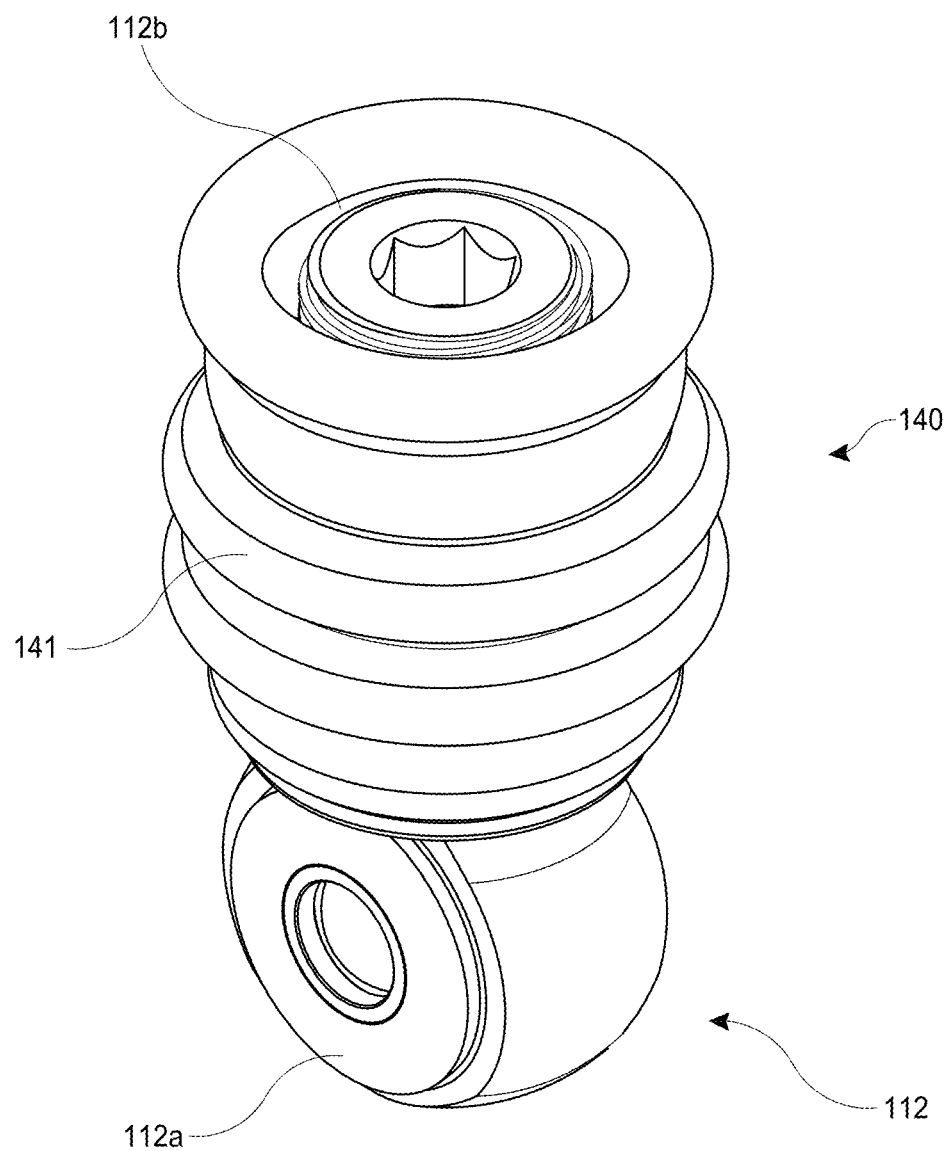
FIG. 9 illustrates a lower component of the actuator of FIGS. 1-3B.
Figure 10:
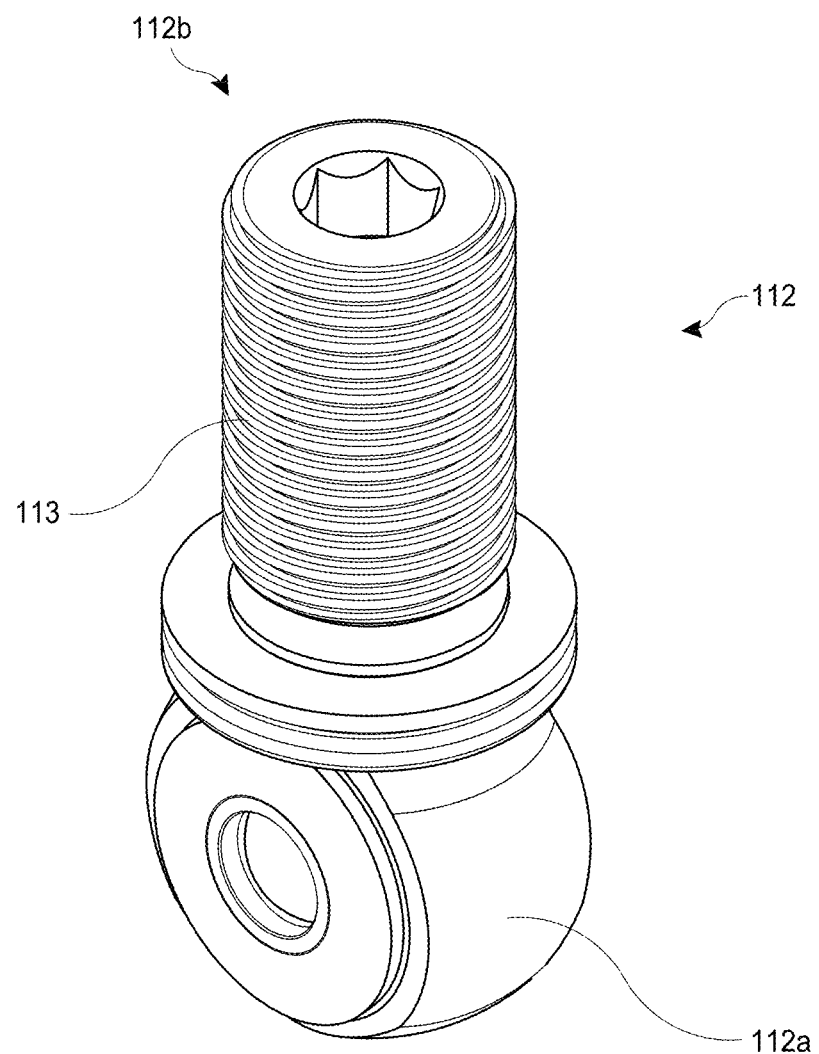
FIG. 10 illustrates the lower component of FIG. 9 with an outer housing removed.
Figure 11:
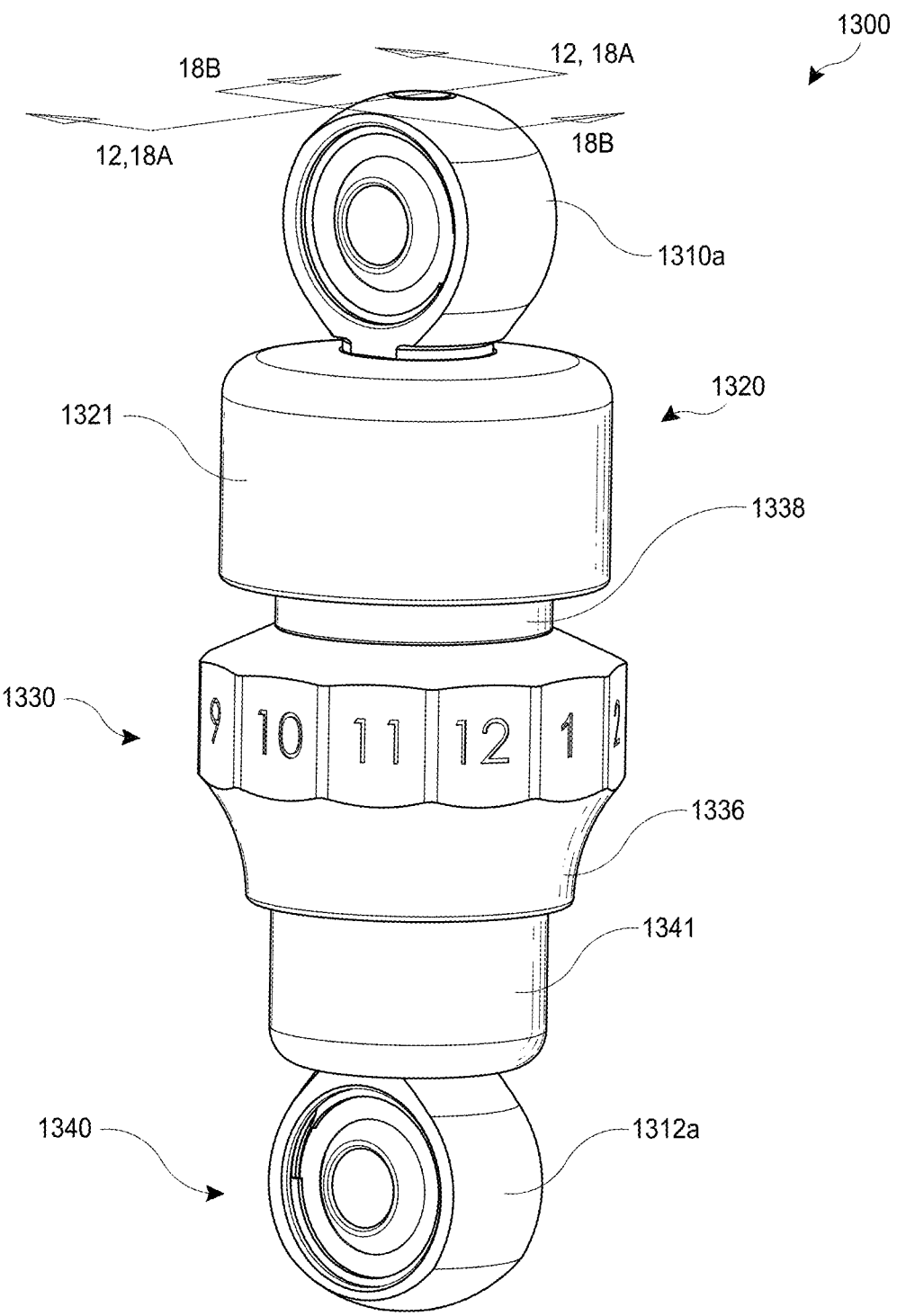
FIG. 11 illustrates a perspective view of an example embodiment of an actuator or adjustment mechanism.

FIGS. 1-3B illustrate an example embodiment of an actuator or adjustment mechanism 100. In some embodiments, the actuator 100 can be incorporated into a prosthetic joint, for example, a prosthetic ankle. As shown in the exploded views of FIGS. 3A-3B, in the illustrated embodiment, the actuator 100 includes an upper component 120, a lower component 140, and a central component 130. As also shown in FIGS. 4-6, the upper component 120 includes an upper connector 110 and an outer housing 121. As also shown in FIGS. 9-10, the lower component 140 includes a lower connector 112 and an optional outer housing or bellows 141. The upper 110 and lower 112 connectors extend from opposite ends of the actuator 100. In some embodiments, the upper 110 and lower 112 connectors are ball joint rod end bearings. The upper connector 110 has a ball joint 110a at one end of the upper connector 110 and a threaded shaft 111 (shown in FIG. 6) extending between the ball joint 110a and a distal end 110b at an opposite end of the upper connector 110. The lower connector 112 has a ball joint 112a at one end of the lower connector 112 and a threaded shaft 113 (shown in FIG. 10) extending between the ball joint 112a and a proximal end 112b at an opposite end of the lower connector 112. The ball joints 110a, 112a are oriented at the top and bottom, respectively, of the actuator 100, and the ends 110b, 112b are disposed opposite each other along a longitudinal axis (e.g., central axis or symmetrical axis) of the actuator 100. In one embodiment, one of the connectors 110, 112 can have clockwise threads while the other of the connectors 110, 112 can have counterclockwise threads.

As shown in FIG. 5, the outer housing 121 of the upper component 120 is hollow, cylindrical or generally cylindrical, and disposed around at least a portion of the upper connector 110, for example, around the threaded shaft 111. The outer housing 121 can be integrally formed with or attached to the upper connector 110. For example, the outer housing 121 can be attached to the upper connector 110 just below the ball joint 110a. With continued reference to FIG. 5, the threaded shaft 111 of the upper connector 110 can extend through the outer housing 121 such that a circumferential annulus 115 is defined between an inner surface of the outer housing 121 and a threaded surface of the upper connector 110.

Figure 1:
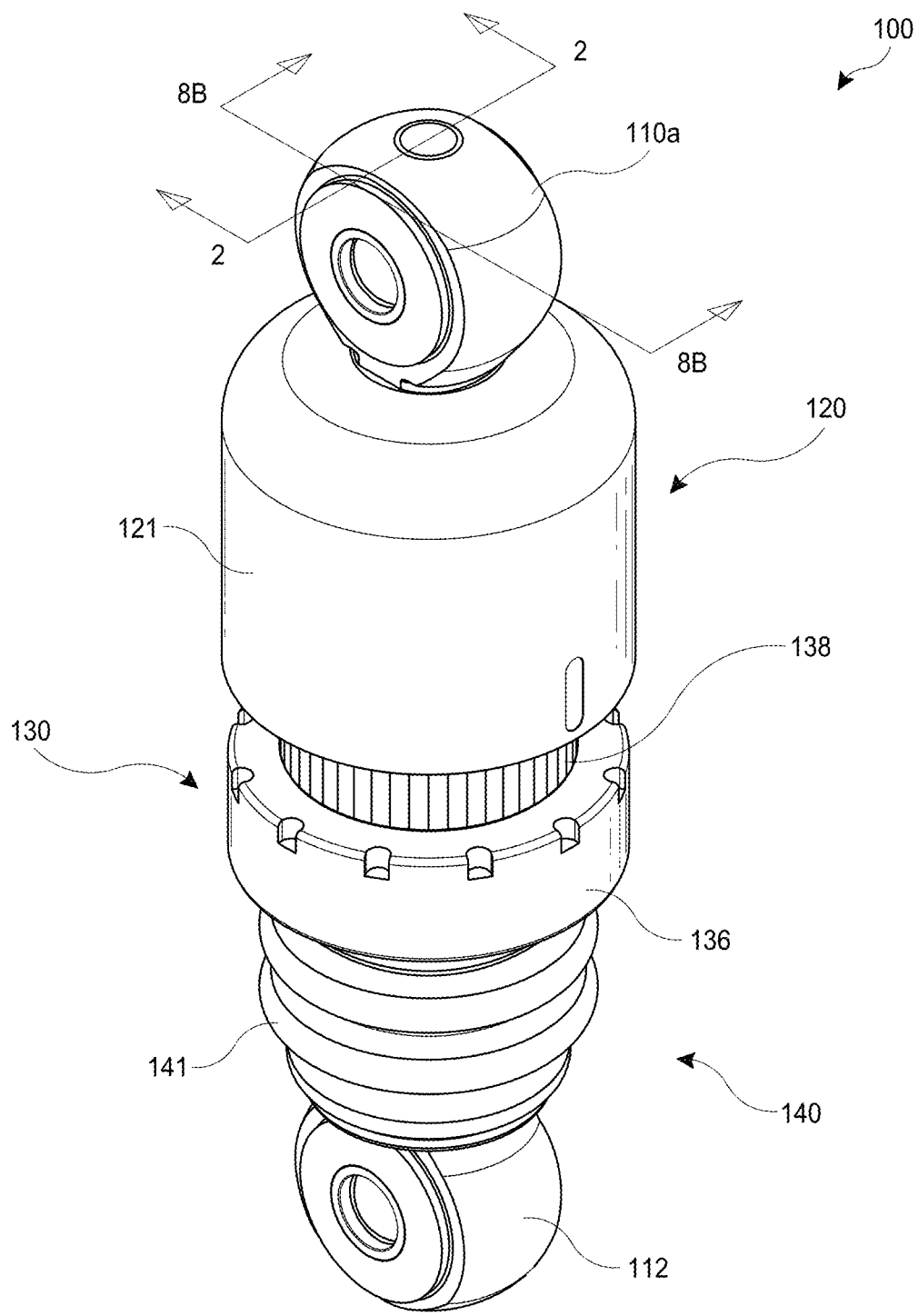
FIG. 1 illustrates a perspective view of an example embodiment of an actuator or adjustment mechanism.
Figure 2:
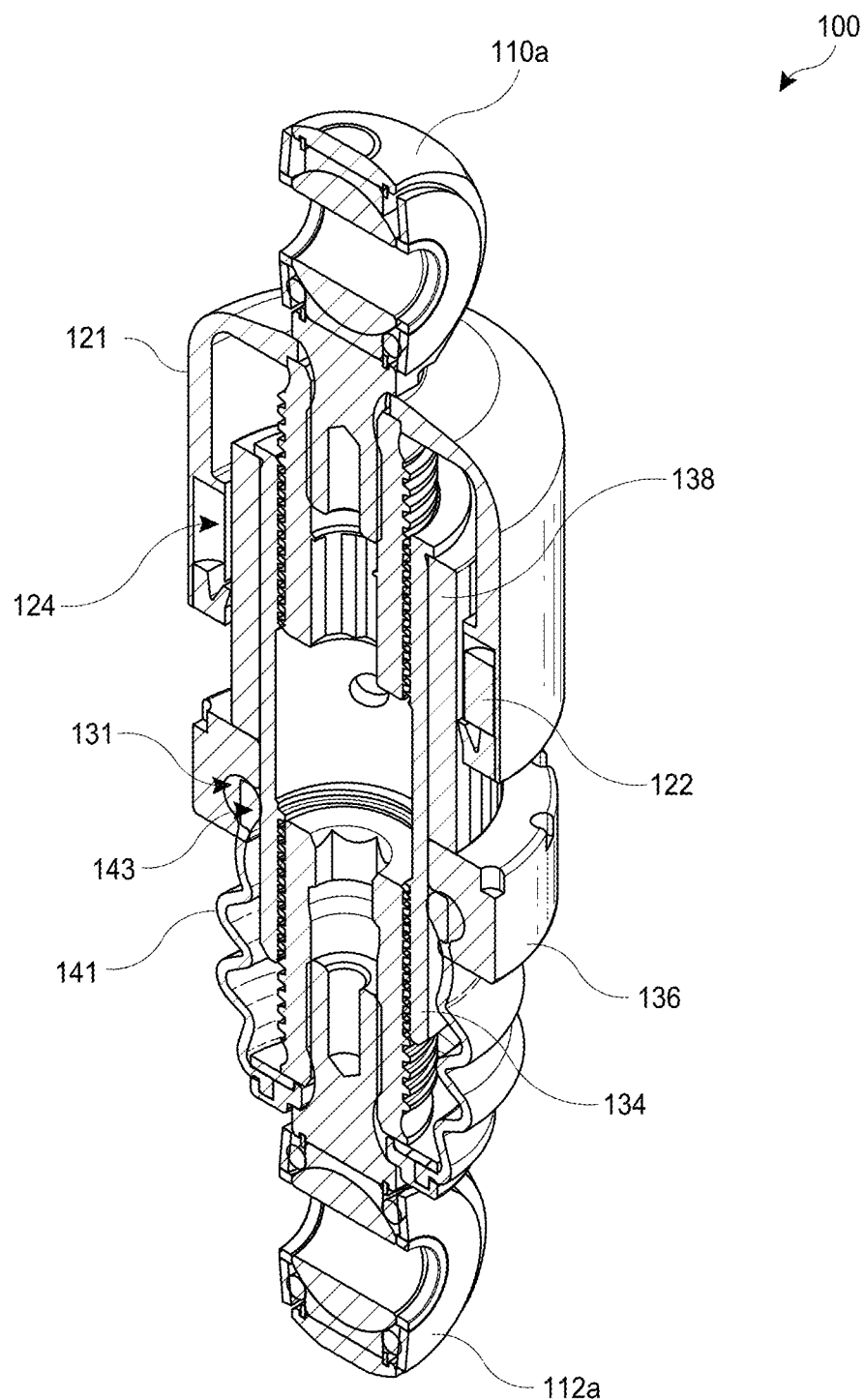
FIG. 2 illustrates a cross-sectional view of the actuator of FIG. 1.
Figure 3A:
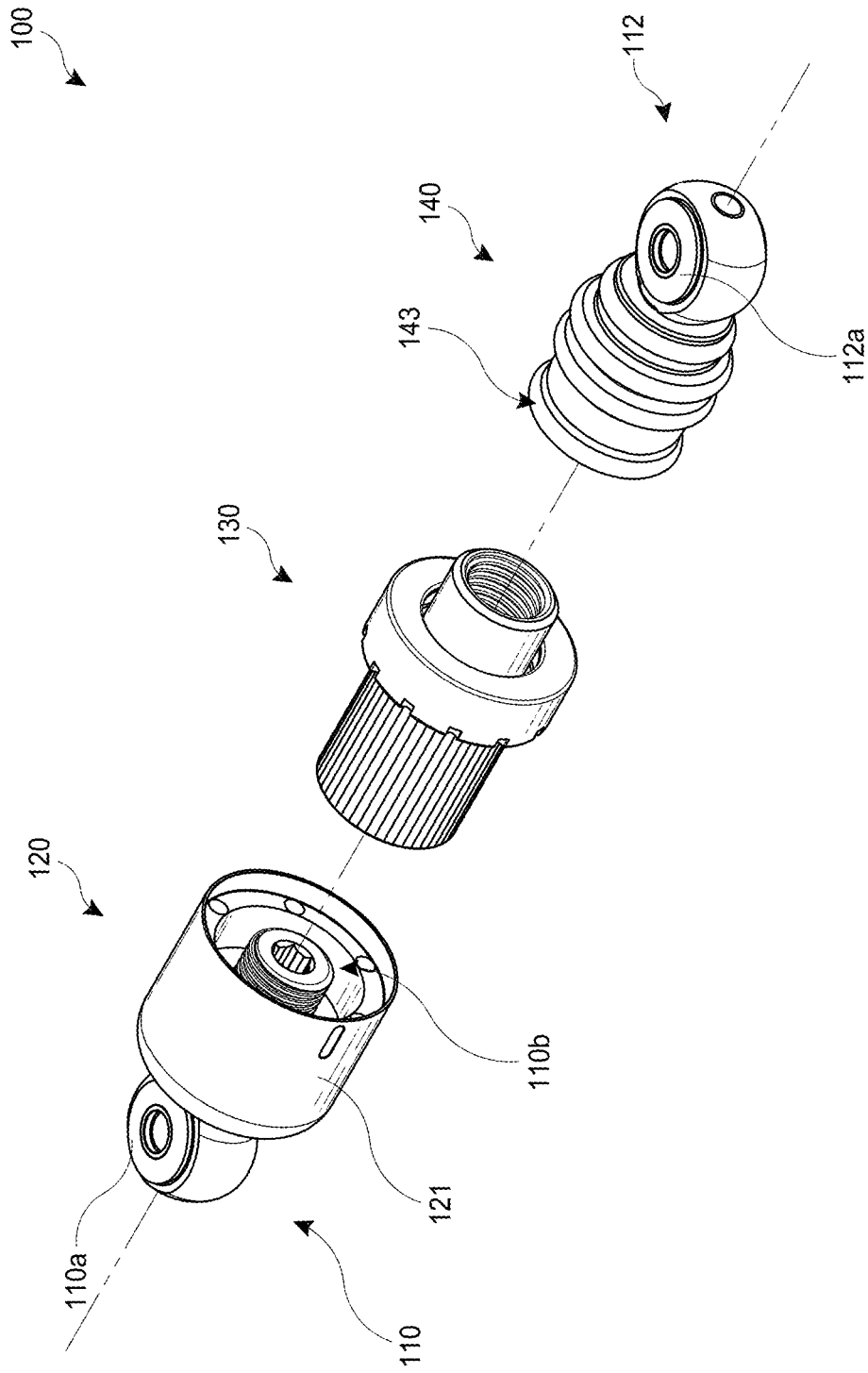
FIGS. 3A-3B illustrate exploded views of the actuator of FIGS. 1-2.
Figure 3B:
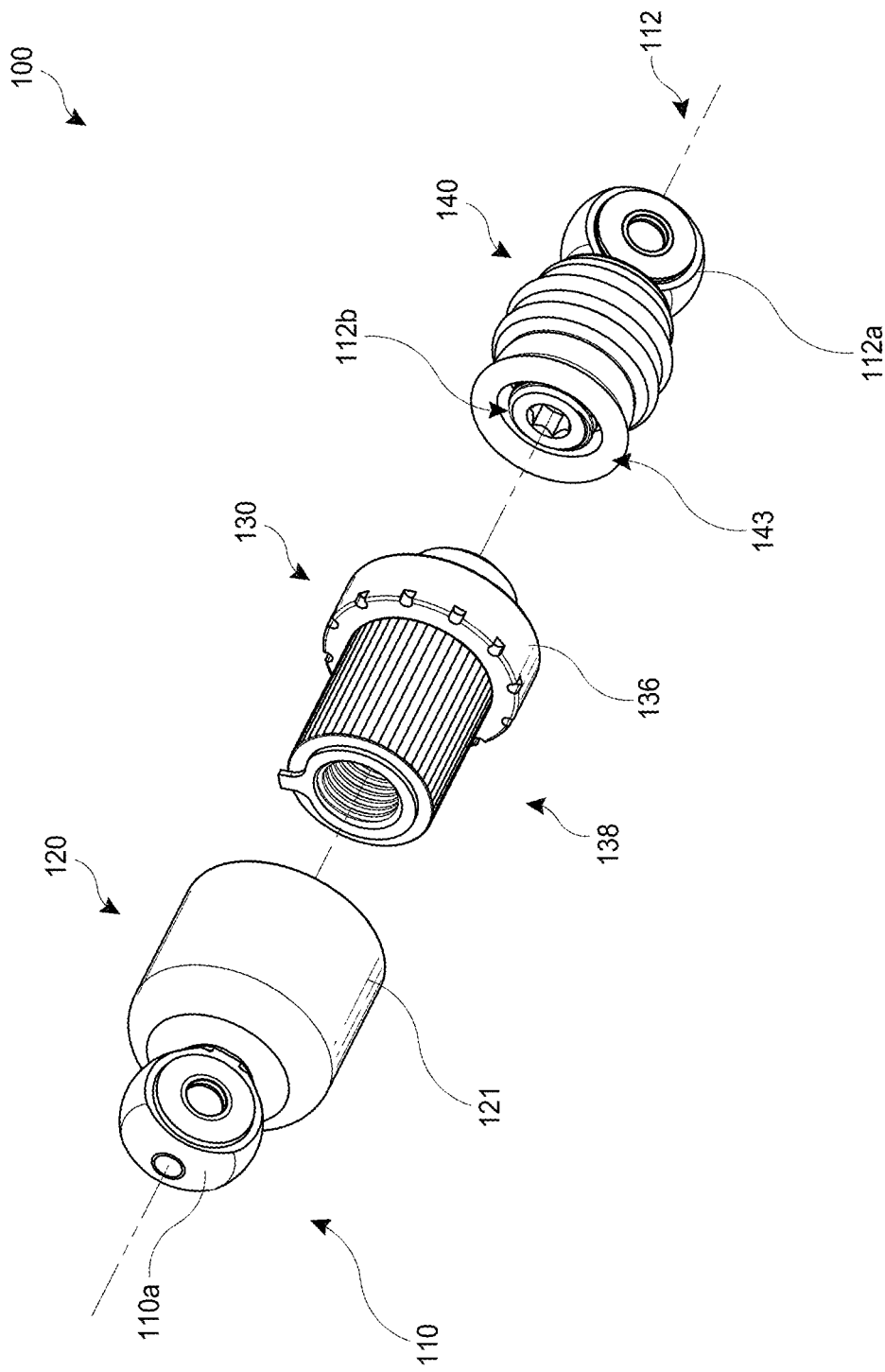
Figure 7:
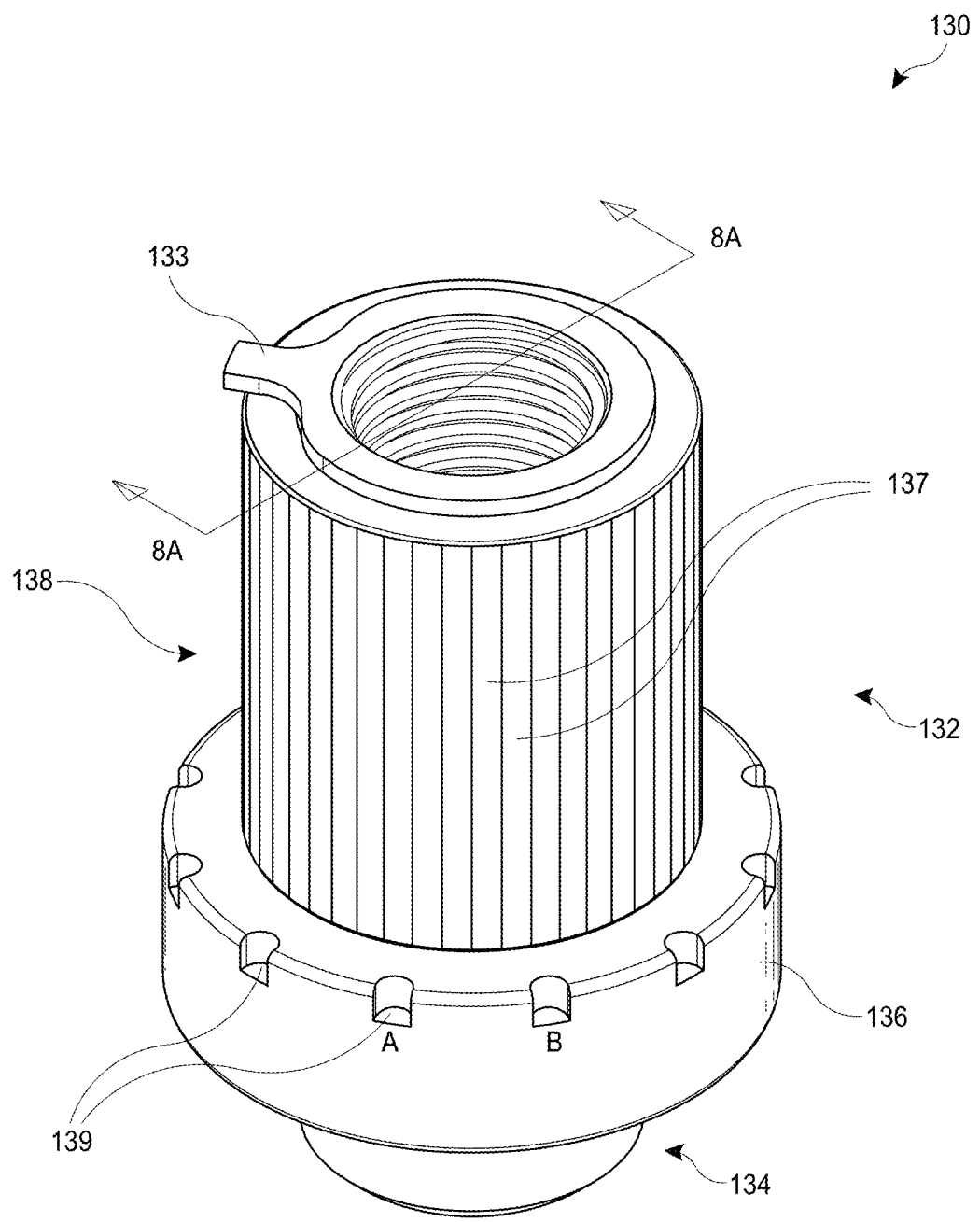
FIG. 7 illustrates a central component of the actuator of FIGS. 1-3B.
Figure 8A:
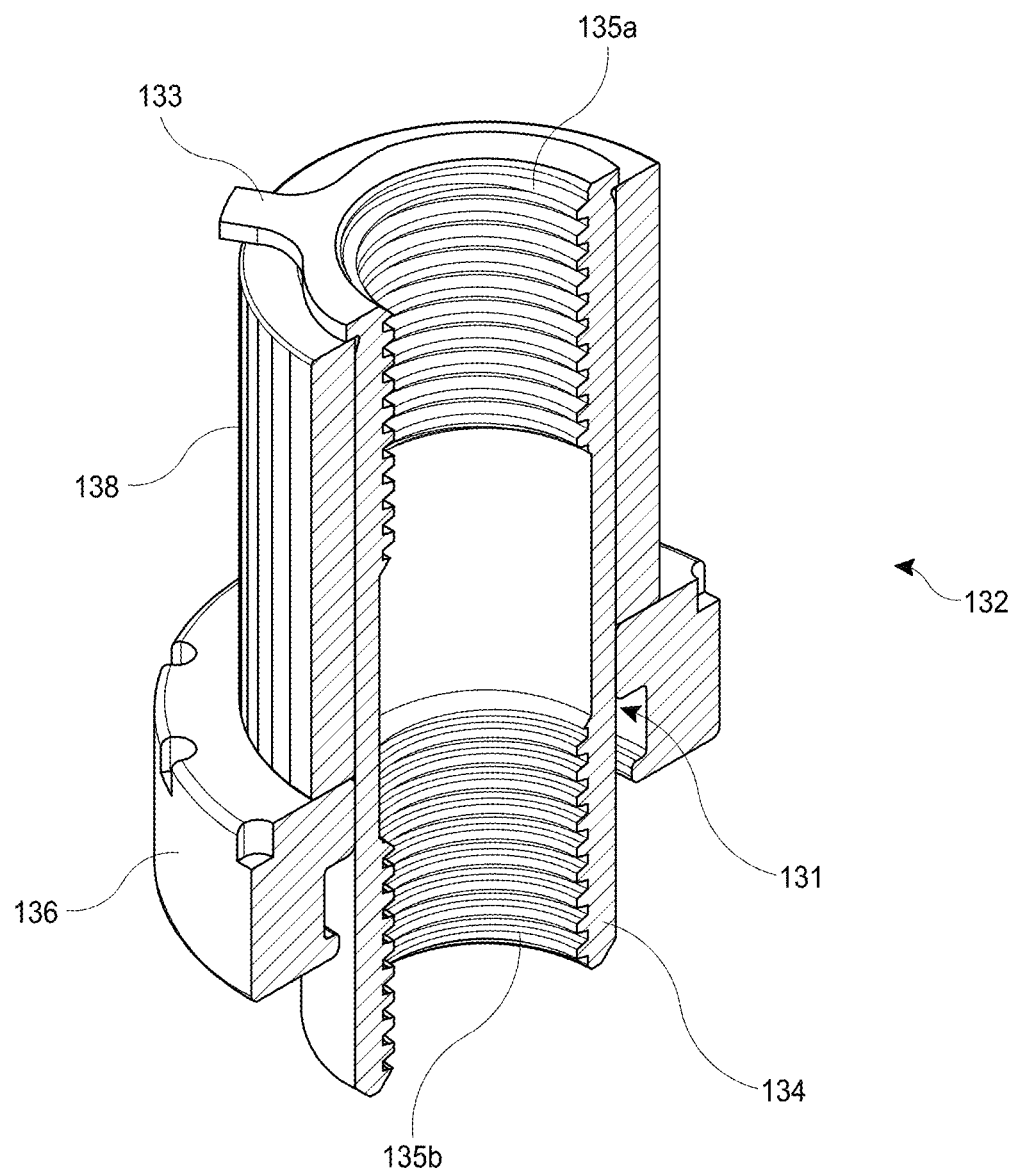
FIG. 8A illustrates a cross-sectional view of the central component of FIG. 7.

As shown in FIGS. 7-8A, in the illustrated embodiment, the central component 130 has an outer shell 132 and an inner shaft 134. In the illustrated embodiment, the outer shell 132 has a base 136 and a cylindrical shaft 138. The inner shaft 134 is disposed within and can be permanently or removably coupled to the outer shell 132. In the illustrated embodiment, the base 136 is generally circular. However, the shape of the base is not limiting. For example, the base can have a triangular or polygon-shaped perimeter, or have other shapes. The base 136 can be attached or positioned distal to the cylindrical shaft 138. For example, the base 136 can be attached to and/or positioned adjacent a distal end of the shaft 138. In some embodiments, an inner surface of the base 136 has a recess 131 (as shown in, for example, FIG. 8A). As shown in FIG. 2, a top portion 143 of the optional outer housing 141 of the lower component 140 is disposed in the recess 131. As shown in FIG. 8A, at least a portion of the inner shaft 134 is internally threaded. In the illustrated embodiment, the inner shaft 134 includes an upper internally threaded portion 135a and a lower internally threaded portion 135b. In some embodiments, the central component 130 can be a single component without a separate outer shell 132 and inner shaft 134.

Returning to FIG. 2, the internally threaded inner shaft 134 receives and threadedly engages the threaded shafts 111, 113 (see FIGS. 6, 10) of the upper connector 110 and the lower connector 112, respectively. For example, in the illustrated embodiment, the upper internally threaded portion 135a (shown in FIG. 8A) threadedly engages the threaded shaft 111 of the upper connector 110, and the lower internally threaded portion 135b (shown in FIG. 8A) threadedly engages the threaded shaft 113 of the lower connector 112. The cylindrical shaft 138 of the central component 130 is at least partially disposed within the circumferential annulus 115 in the upper component 120 between the outer housing 121 and the threaded shaft 111 of the upper connector 110. In use, the central component 130 can be rotated to adjust a height or length of the actuator 100. Rotation of the central component 130 is translated into linear motion of the connectors 110, 112 and causes the distance between the ends 110b, 112b of the connectors 110, 112 to increase or decrease, depending on the direction of rotation of the central component 130.

Figure 8B:
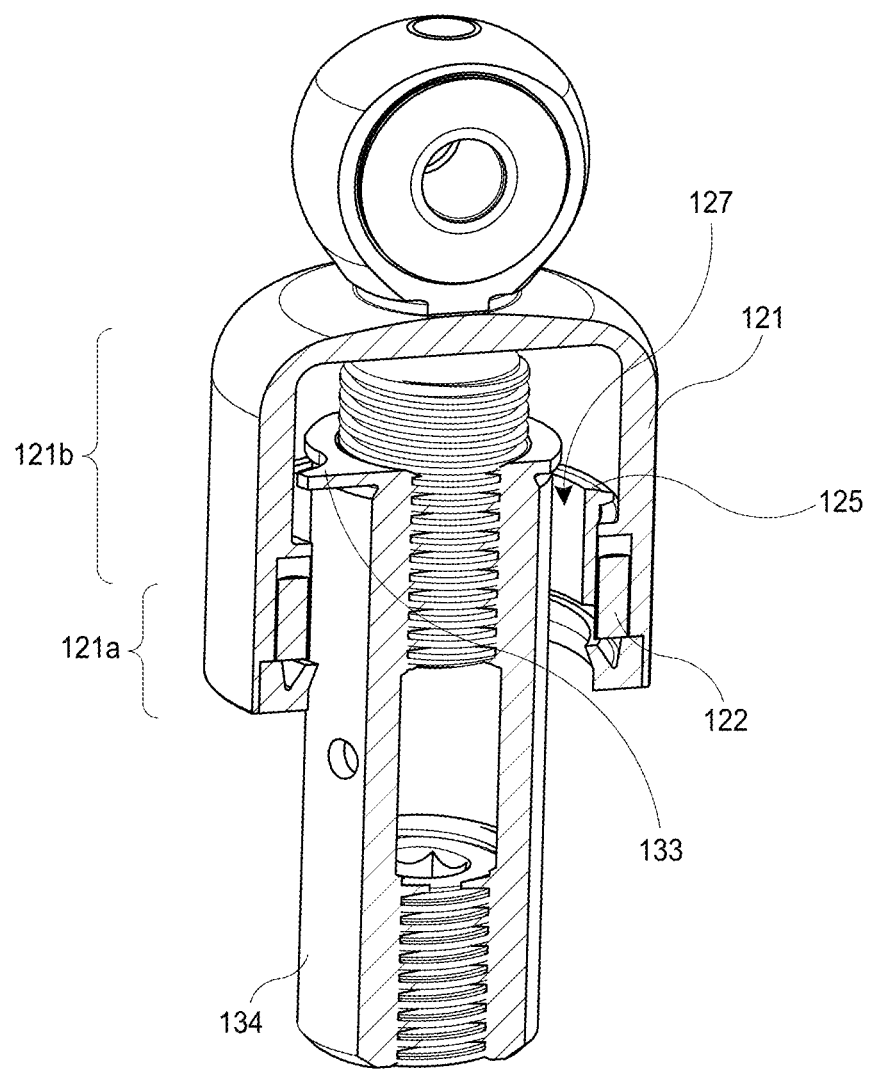
FIG. 8B illustrates a partial cross-sectional view of the upper and central components of FIGS. 7 and 8A.

With continued reference to FIGS. 7-8A, in some embodiments, the inner shaft 134 can have a tab 133 extending outwardly from an upper end of the inner shaft 134. The tab 133 can act as a travel limit during assembly and/or use. As shown in FIG. 8B (in which the outer shell 132 is removed for clarity), the tab 133, or a portion of the upper end of the inner shaft 134 including the tab 133, has a larger diameter than an inner surface of a lower portion 121a of the outer housing 121. An inner surface of an upper portion 121b of the outer housing 121 can have a larger diameter than the inner surface of the lower portion 121a to accommodate the tab 133. The inner surface of the lower portion 121a of the outer housing 121 can include a groove or channel 127. During assembly, the groove or channel 127 accommodates the tab 133 and allows the tab 133, and therefore the central component 130, to move upwards into the outer housing 121 of the upper component 120. During use, the tab 133 no longer aligns with the groove or channel 127. If the central component 130 is rotated relative to the upper component 120, for example, to adjust a height of the actuator as described herein, such that the central component 130 moves away from the upper component 120, the central component 130 can rotate relative to the upper component 120 until the tab 133 contacts an upper ledge 125 of the lower portion 121a of the outer housing 121. The upper ledge 125 has an internal diameter configured to prevent the tab 133 from moving further away from the upper component 120. The tab 133 contacting the upper ledge 125 therefore acts as a stop such that the upper and central components 120, 130 cannot be unscrewed from each other beyond a certain extent. In other embodiments, the outer housing 121 can comprise a plurality of components instead of or in addition to the groove/channel 127 for assembly purposes, which will be described in greater detail below.

Returning to FIGS. 5-6, the outer housing 121 of the upper component 120 includes one or more magnets 122. The outer housing 121 can include one or more longitudinally or axially extending grooves, channels, or apertures 124, for example as shown in FIGS. 2 and 5. Each of the channels 124 can receive and contain a cylindrical or bar magnet 122. In the illustrated embodiment, the outer housing 121 includes three magnets 122, as shown in FIG. 6. The upper component 120 can include an end cap 123 coupled to an end of the outer housing 121 nearest the end 110b of the connector 110 or away from the ball joint 110a, for example as shown in FIGS. 5 and 6, to help hold and secure the magnets 122 within the outer housing 121. As shown in FIG. 7, the central component 130, for example, the cylindrical shaft 138 of the outer shell 132, includes one or more corresponding cylindrical or bar magnets. The cylindrical shaft 138 can itself be formed of one or more magnets or can include one or more magnets attached to the cylindrical shaft 138. For example, in the illustrated embodiment, the cylindrical shaft 138 includes a plurality of adjacent bar magnets 137 disposed around an outer perimeter or surface of the cylindrical shaft 138. Although in the illustrated embodiment the magnets 137 extend around the entirety of the cylindrical shaft 138 and are adjacent one another, in other embodiments the magnets 137 may extend around only a portion of the cylindrical shaft 138 and/or may be spaced from each other. Additionally, in some embodiments, the cylindrical shaft 138 and/or magnet 137 can be a single piece of material that may be magnetized in steps to have different polarities as described below.

The magnets 122 in the outer housing 121 and magnets 137 on the cylindrical shaft 138 can have opposing poles such that the magnets attract each other. When the central component 130 is rotated relative to the outer housing 121 such that the magnets 137 in the central component 130 are aligned with the magnets 122 in the outer housing 121, the attraction between the magnets locks or substantially locks the position of the central component 130 relative to the outer housing 121 and therefore locks or substantially locks the height or length of the actuator 100. If desired, a user can overcome the magnetic force between the magnets to rotate the central component 130 relative to the outer housing 121 and adjust the height of the actuator 100 (e.g., by rotating the central component 130 relative to the upper component 120 with a rotational force that is higher than the magnetic force between the magnets).

In the illustrated embodiment, adjacent magnets 137 in the central component 130 have alternating polarities. In some embodiments, instead of a plurality of adjacent magnets 137, the cylindrical shaft 138 and/or a magnet coupled to and/or disposed around the cylindrical shaft 138 can be a single piece of material that is magnetized in steps to form a plurality of adjacent sections of different, e.g., alternating, polarities. The magnets 122 in the upper component 120 can have split polarities. For example, as shown in FIG. 6, half 122a of each magnet 122 can have one polarity and the other half 122b of each magnet 122 can have the opposite polarity. The central component 130 can be rotated relative to the upper component 120 such that the magnets 122 in the upper component 120 are aligned with magnets 137 in the central component 130 of the same or opposing polarity. The attraction between magnets 122 and magnets 137 of opposing polarity can be overcome by the user physically rotating the central component 130. The user can therefore rotate the central component 130 to adjust the distance between the connectors 110, 112 and therefore the height or length of the actuator 100. Once the desired height is achieved, the user can lock the actuator 100 by, if needed, slightly further rotating the central component 130 until the magnets 122 are aligned with the nearest magnets 137 of opposing polarity.

In some embodiments, the base 136 can include one or more markings 139, some or all of which may be labeled (e.g., with letters A and B in FIG. 7). In the illustrated embodiment, markings 139 are disposed around the entirety circumference of the base 136 at even intervals; however, in other embodiments, the markings 139 may have unequal spacing, the marks 139 may not extend around the entirety of the circumference of the base 136, and/or the base 136 may include more or fewer markings 139 than shown. The outer housing 121 of the upper component 120 can include one or more markings 129, for example as shown in FIG. 4. The markings 129 and 139 can be arranged and configured such that alignment of marking(s) 129 with a specific marking (or specific markings) 139 indicates a locked or unlocked position of the actuator 100. Additionally or alternatively, in some embodiments, the markings 129 and/or 139 can be arranged and configured such that alignment of marking(s) 129 with a specific marking (or specific markings) 139 indicates a height of the actuator 100.

In some embodiments, the actuator 100 includes or acts as a stepper magnet. The central component 130 can be rotated among discrete locations or positions to adjust the length of the actuator 100, thereby, for example, adjusting the heel height of a prosthetic foot that incorporates the actuator 100. When the central component 130 is positioned in one of the discrete locations, attraction between the magnets 122, 137 holds the rotational position of the central component 130 in a locked position.

FIGS. 11-20 illustrate another embodiment of an actuator or adjustment mechanism 1300 having the same or similar features as the actuator 100 of FIGS. 1-10 except as described herein. Reference numerals of same or similar components of the actuators 100 and 1300 have the same last two digits. Accordingly, features of the actuator 1300 can be incorporated into features of the actuator 100 and features of the actuator 100 can be incorporated into features of the actuator 1300, for example, the upper component (also referred to as a first actuator assembly) 1320, and the central 1330 and lower 1340 components (also referred to collectively as a second actuator subassembly).

Figure 14:
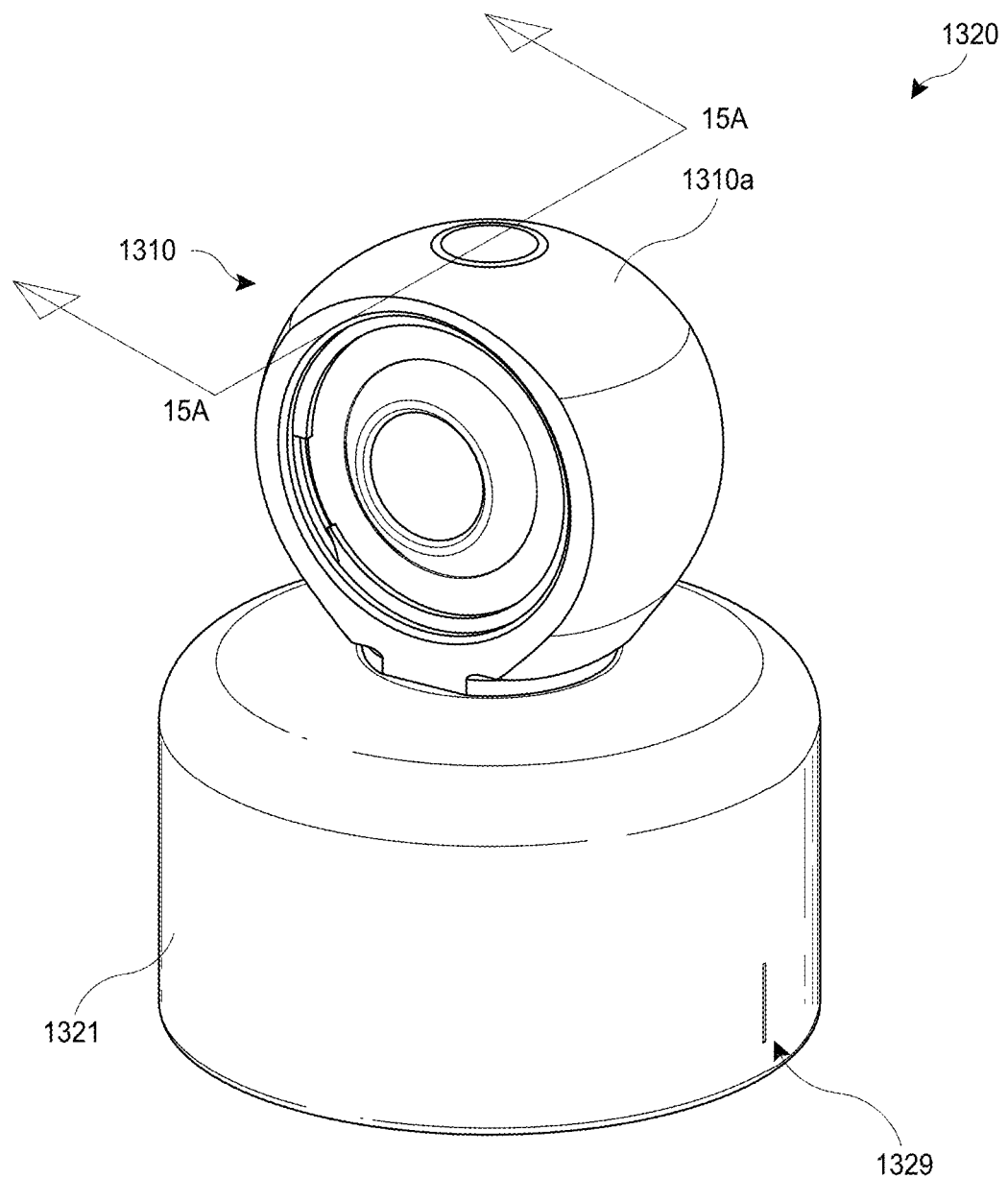
FIG. 14 illustrates an upper component of the actuator of FIGS. 11-13B.
Figure 15A:
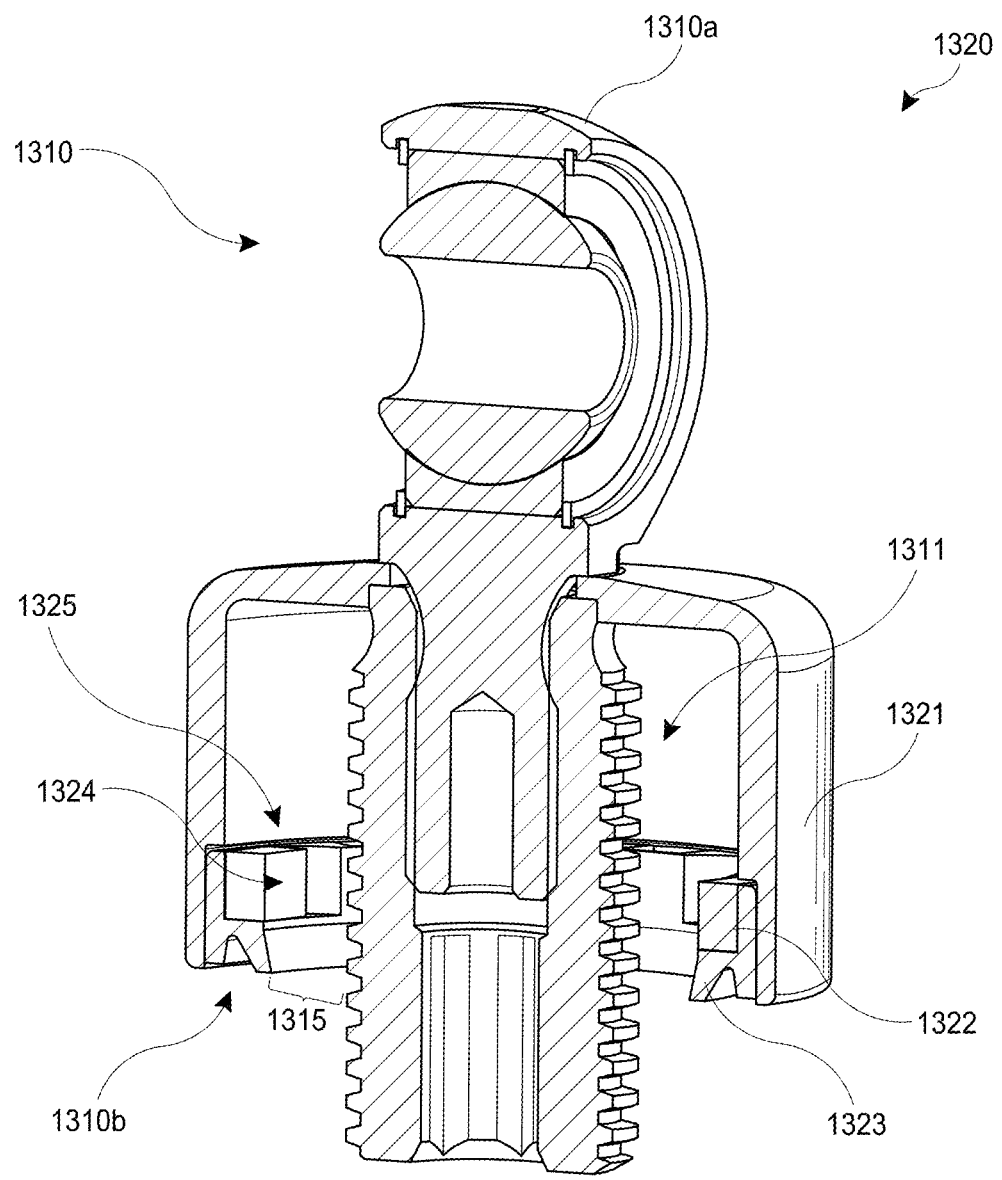
FIG. 15A illustrates a cross-sectional view of the upper component of FIG. 14.
Figure 15B:
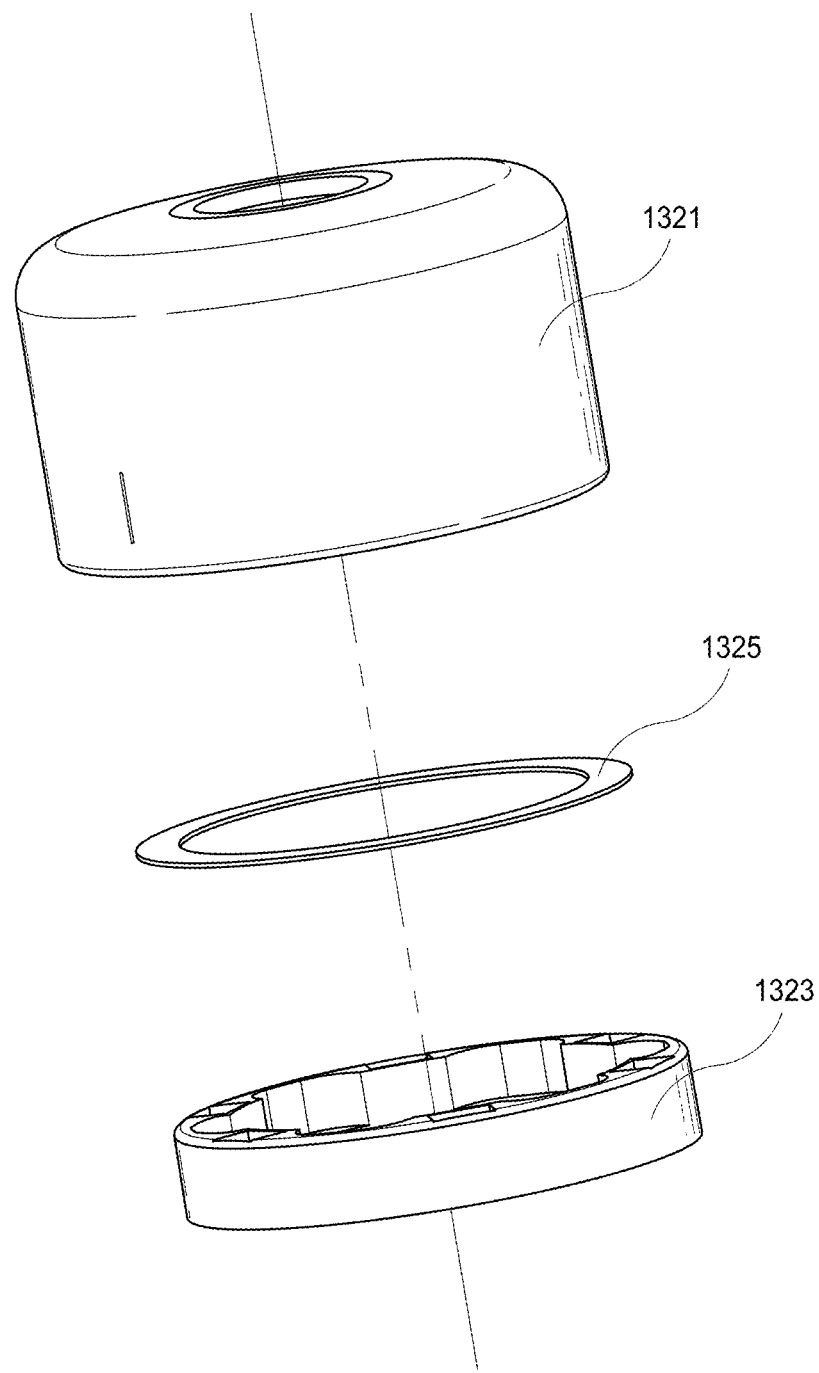
FIG. 15B illustrates an exploded view of an outer housing of the upper component of FIG. 14 having an outer housing main body, a washer, and an end cap.
Figure 16:
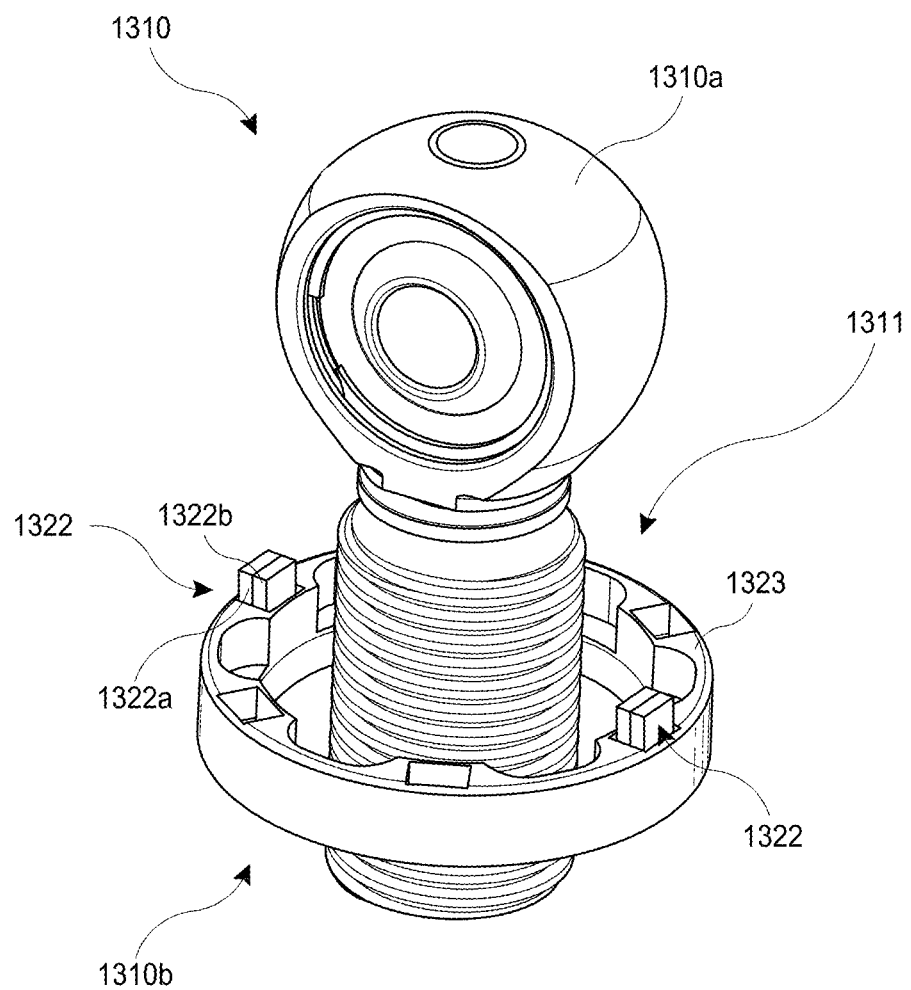
FIG. 16 illustrates the upper component of FIGS. 14-15B with an outer housing removed.

In the illustrated embodiment, as shown in FIG. 15B, which illustrates an exploded view of an outer housing of the upper component 1320 of FIG. 14, the upper ledge 1325 can be formed by a component (e.g., a ring or washer in the illustrated embodiment) that is separately formed from a main body of the outer housing 1321. The outer housing 1321 can include one or more channels 1324 each for receiving a magnet 1322, for example, as shown in FIG. 15A. As shown in FIG. 16, a half 1322a of the magnet 1322 can have one polarity and the other half 1322b of the magnet 1322 can have the opposite polarity. The outer housing main body can have an inner diameter that can accommodate the tab 1333 and can allow the tab 1333, and therefore the central component (also referred to as a first portion of the second actuator subassembly) 1330, to move upwards into the outer housing 1321 during assembly. The washer forming the upper ledge 1325 and the end cap 1323 of the outer housing 1321 can be advanced into the outer housing 1321 following the advancement of the central component 1330. An inner surface of a lower portion 1321a of the outer housing 1321 can have a larger diameter than the inner surface of an upper portion 1321b of the outer housing 1321 as shown. When assembled, the end cap 1323 and the washer forming the upper ledge 1325 are disposed within the lower portion 1321a of the outer housing 1321. The washer forming the upper ledge 1325 can optionally be sandwiched between the end cap 1323 and a lower ledge 1328 of the upper portion 1321b. As shown, the washer forming the upper ledge 1325 has an inner diameter that is smaller than the diameter of the inner surface of the upper portion 1321b. During use, the upper ledge 1325 can act as a stopper for the tab 1333 as described herein. A threaded shaft 1311 of the upper connector 1310 can extend through the outer housing 1321 such that a circumferential annulus 1315 is defined between the end cap 1323 and a threaded surface of the upper connector 1310.

Figure 17:
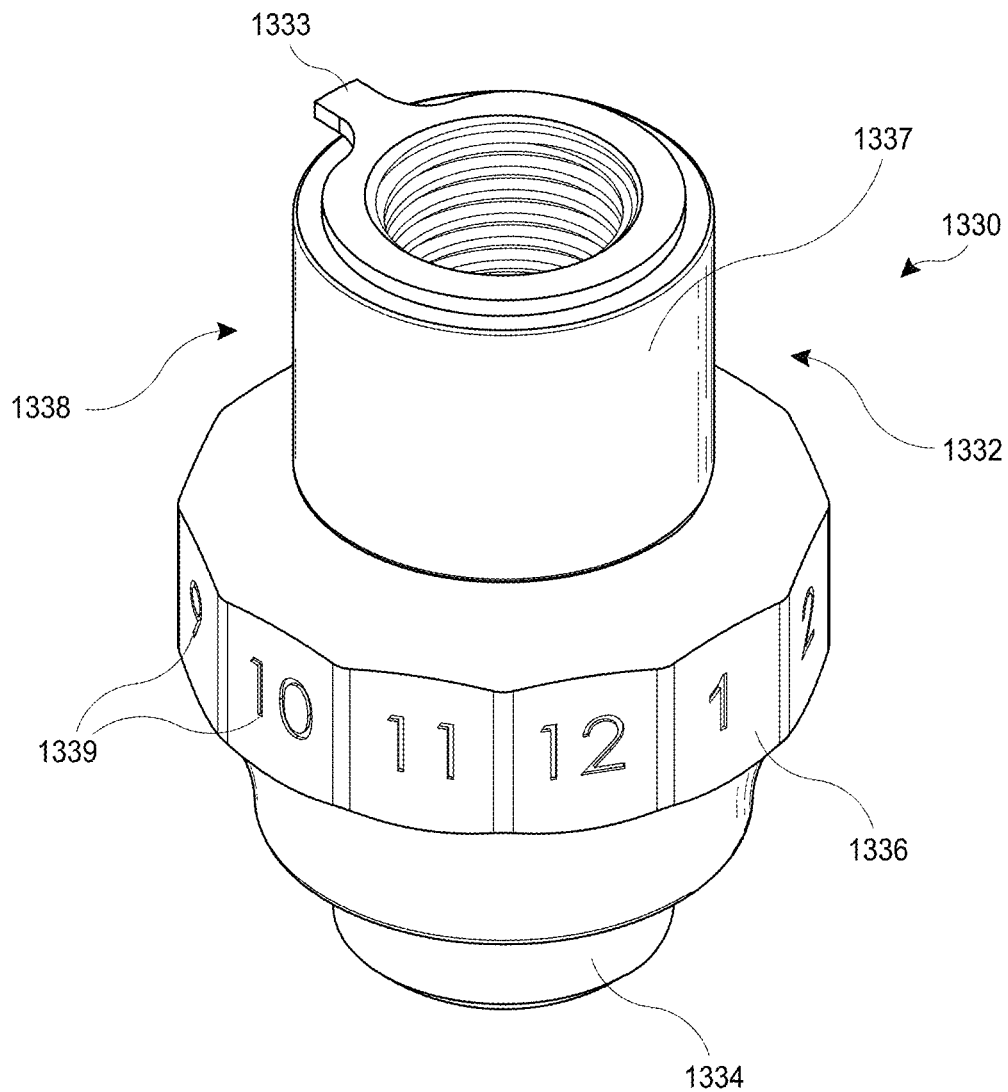
FIG. 17 illustrates a central component of the actuator of FIGS. 11-13B.
Figure 18A:
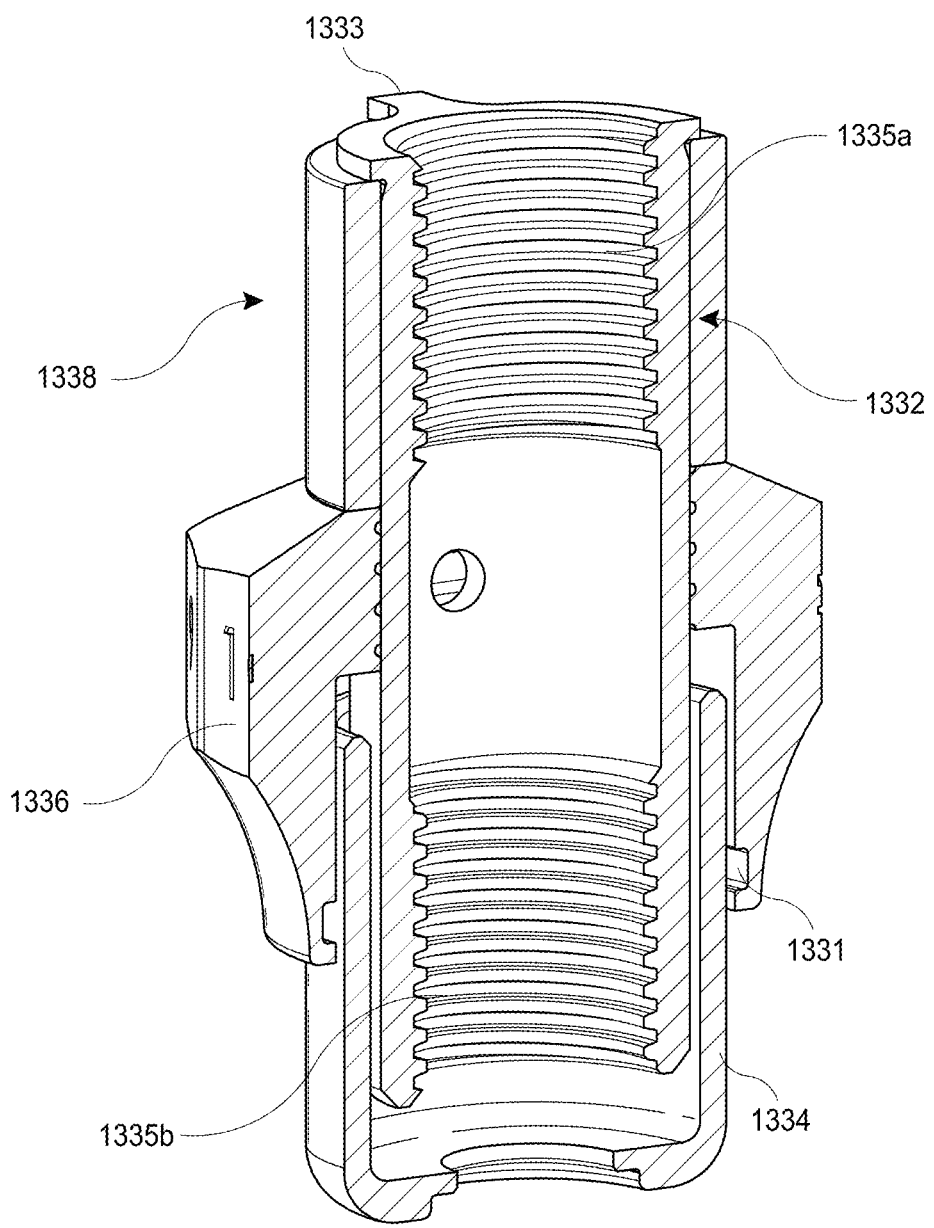
FIG. 18A illustrates a cross-sectional view of the central component of FIG. 17.
Figure 18B:
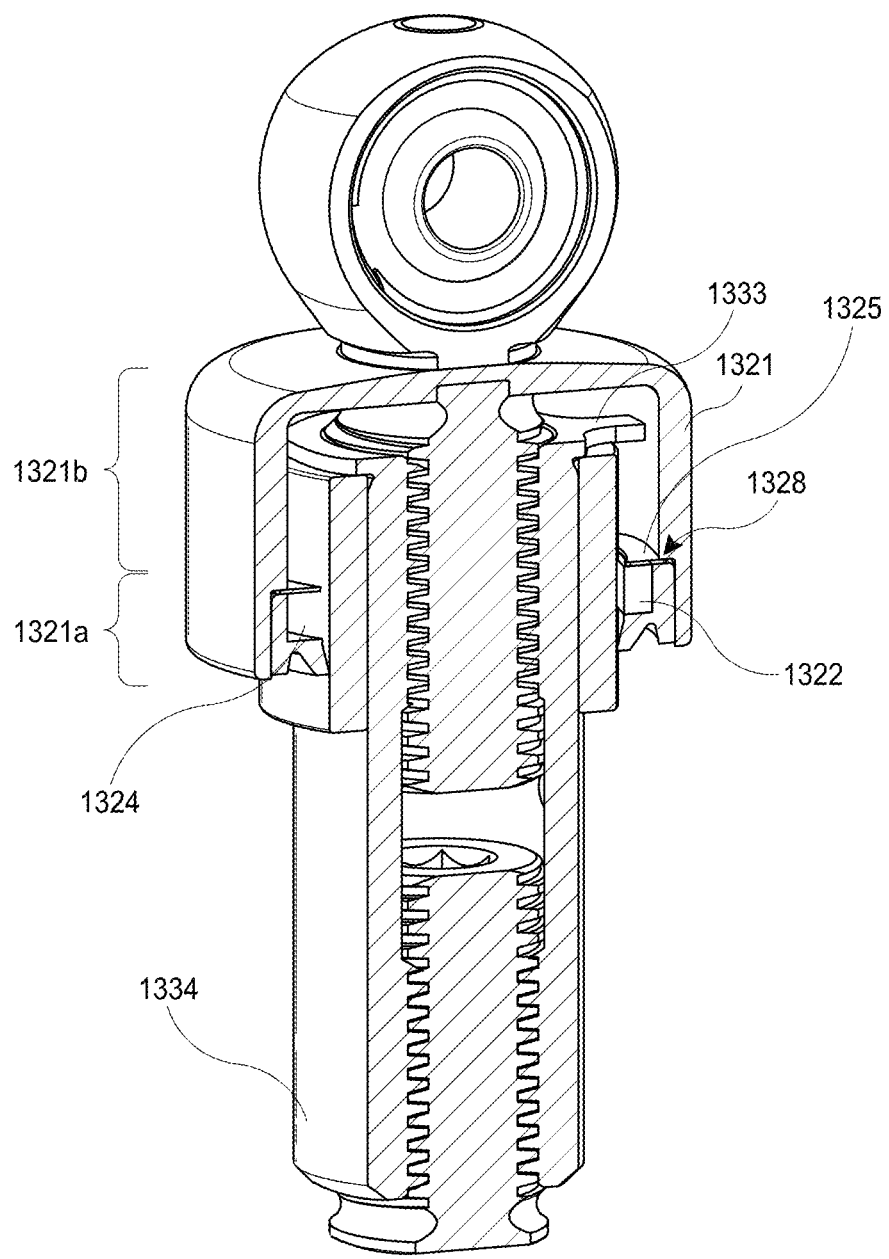
FIG. 18B illustrates a partial cross-sectional view of the upper and central components of FIGS. 17 and 18A.

The outer housing 1321 of the upper component 1320 can include a marking 1329, for example as shown in FIG. 14. The central component 1330 can have an outer shell 1332 and an inner shaft 1334. In the embodiment of FIGS. 11-20, the base 1336 can have markings 1339 of a different kind than those shown in FIG. 7. As shown in FIG. 17, the markings 1339 can be numbers. The number and type of markings shown are for exemplary purposes only and are not limiting. Instead of or in addition to the markings 1339, the actuator 1300 can have markings indicative of the height of the actuator 1300 and/or the travel of the actuator 1300 during adjustment. For example, markings indicative of height can be located on an outer surface of the cylindrical shaft 1338 or an outer surface of the optional outer housing 1341, or on both the outer surfaces of the cylindrical shaft 1338 and optional outer housing 1341. The locations of the markings indicative of height described are not limiting. Non-limiting examples of the markings indicative of height can be at least one of scales, numbers, symbols, or the like. The markings can advantageously allow reproducibility of height settings. The actuator 100 can also include such markings, for example, on the shaft 138 and/or the outer housing 141, indicative of the height and/or travel of the actuator 100. In the illustrated embodiment, the cylindrical shaft 1338 and/or magnet 1337 is a single piece of material that may be magnetized in steps to have different polarities as described above.

Figure 12:
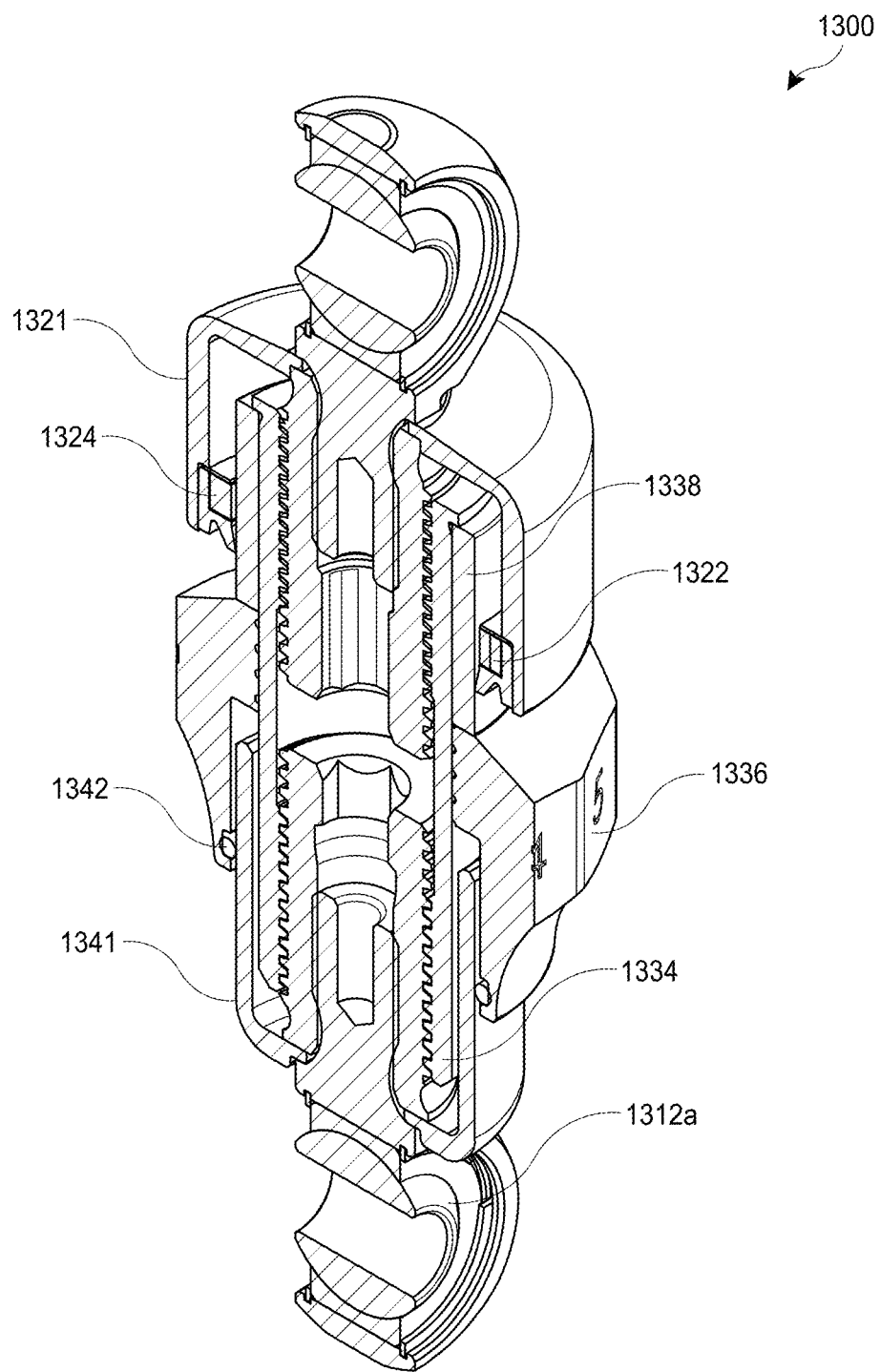
FIG. 12 illustrates a cross-sectional view of the actuator of FIG. 11.
Figure 13A:
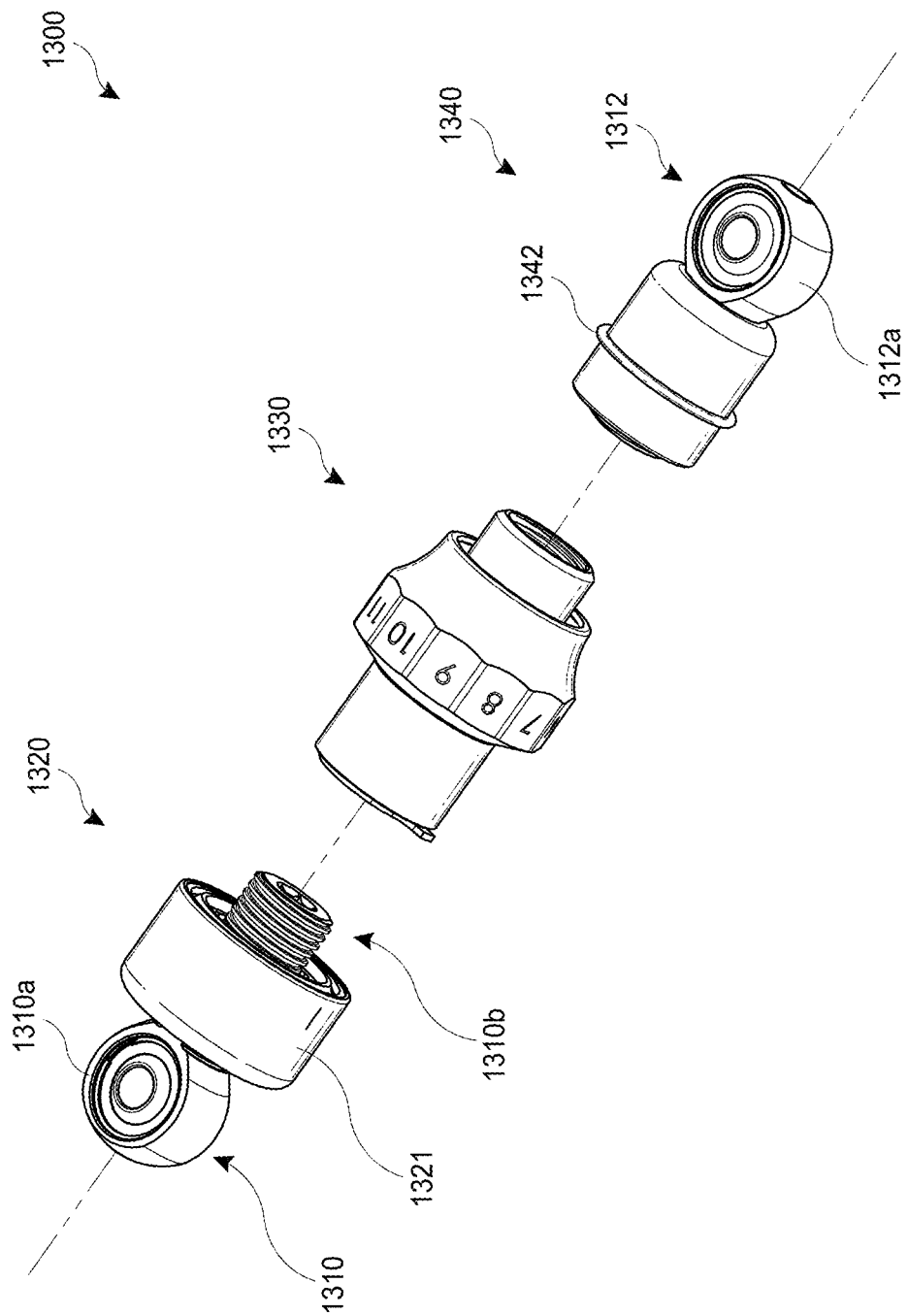
FIGS. 13A-B illustrate exploded views of the actuator of FIGS. 11-12.
Figure 13B:
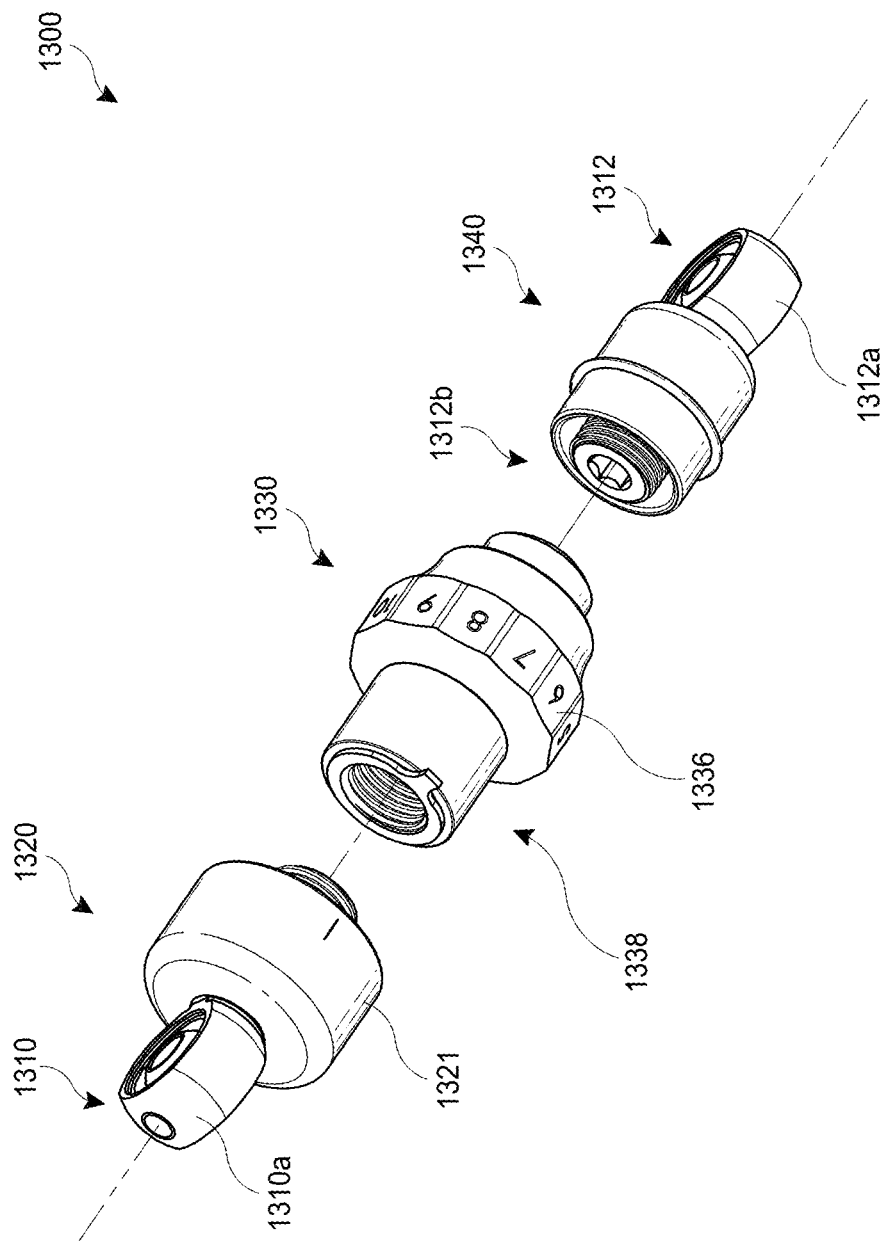
Figure 19:
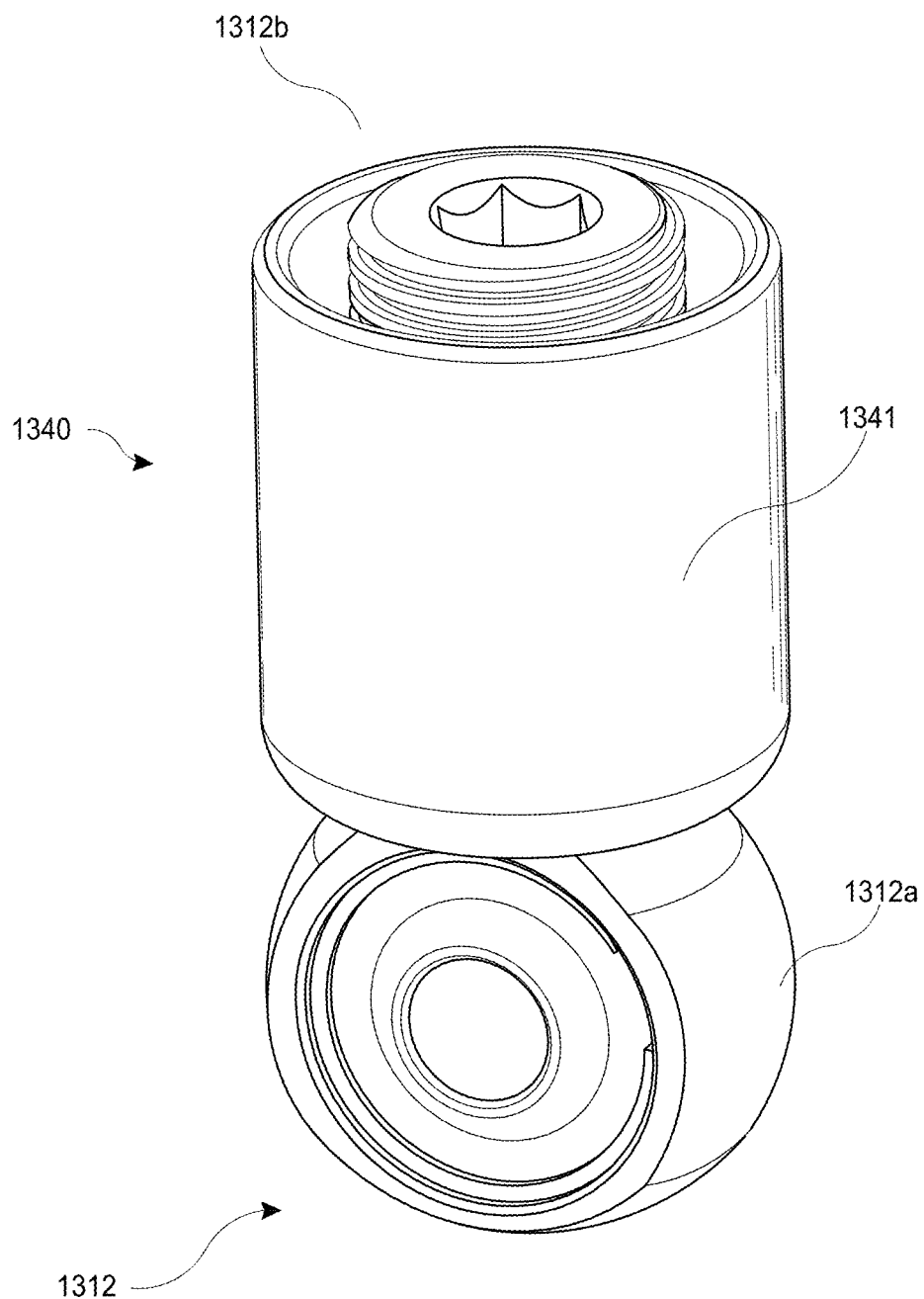
FIG. 19 illustrates a lower component of the actuator of FIGS. 11-13B.
Figure 20:
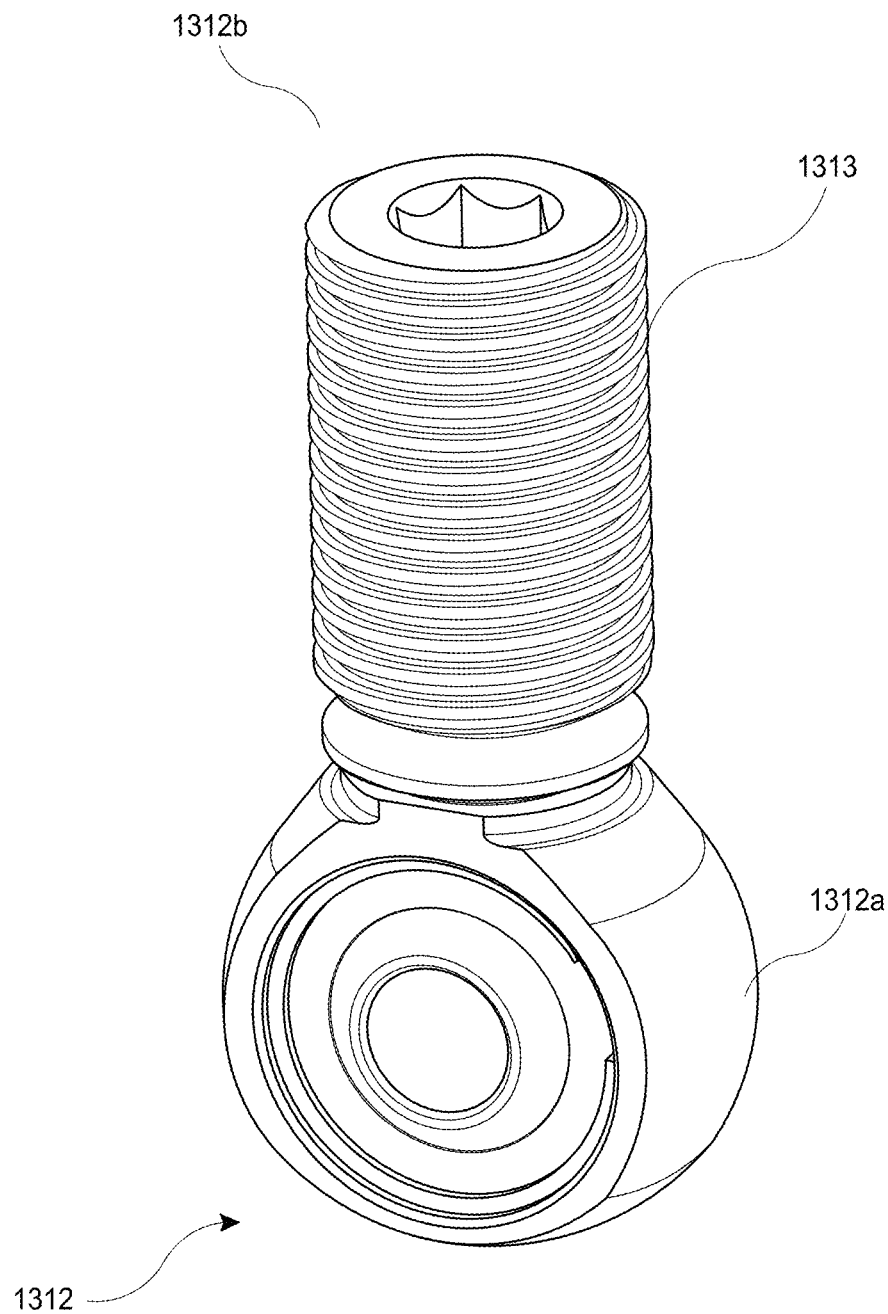
FIG. 20 illustrates the lower component of FIG. 19 with an outer housing removed.

Also as shown in FIG. 19, the optional outer housing 1341 can have a substantially smooth outer surface instead of ridges (e.g., bellows) on an outer surface of the optional outer housing 141 as shown in FIG. 9. The optional outer housing 1341 does not have a top portion that can be retained in the recess 1331 of the base 1336 of the central component 1330. Instead, as shown in FIG. 12, the recess 1331 can accommodate an O-ring 1342 fitted on the outer surface of the optional outer housing 1341, thereby retaining the optional outer housing 1341. The O-ring 1342 allows the lower component (also referred to as a second portion of the second actuator subassembly) 1340 to independently rotate relative to the central component 1330 to adjust the height of the adapter 1300.

Figure 21:
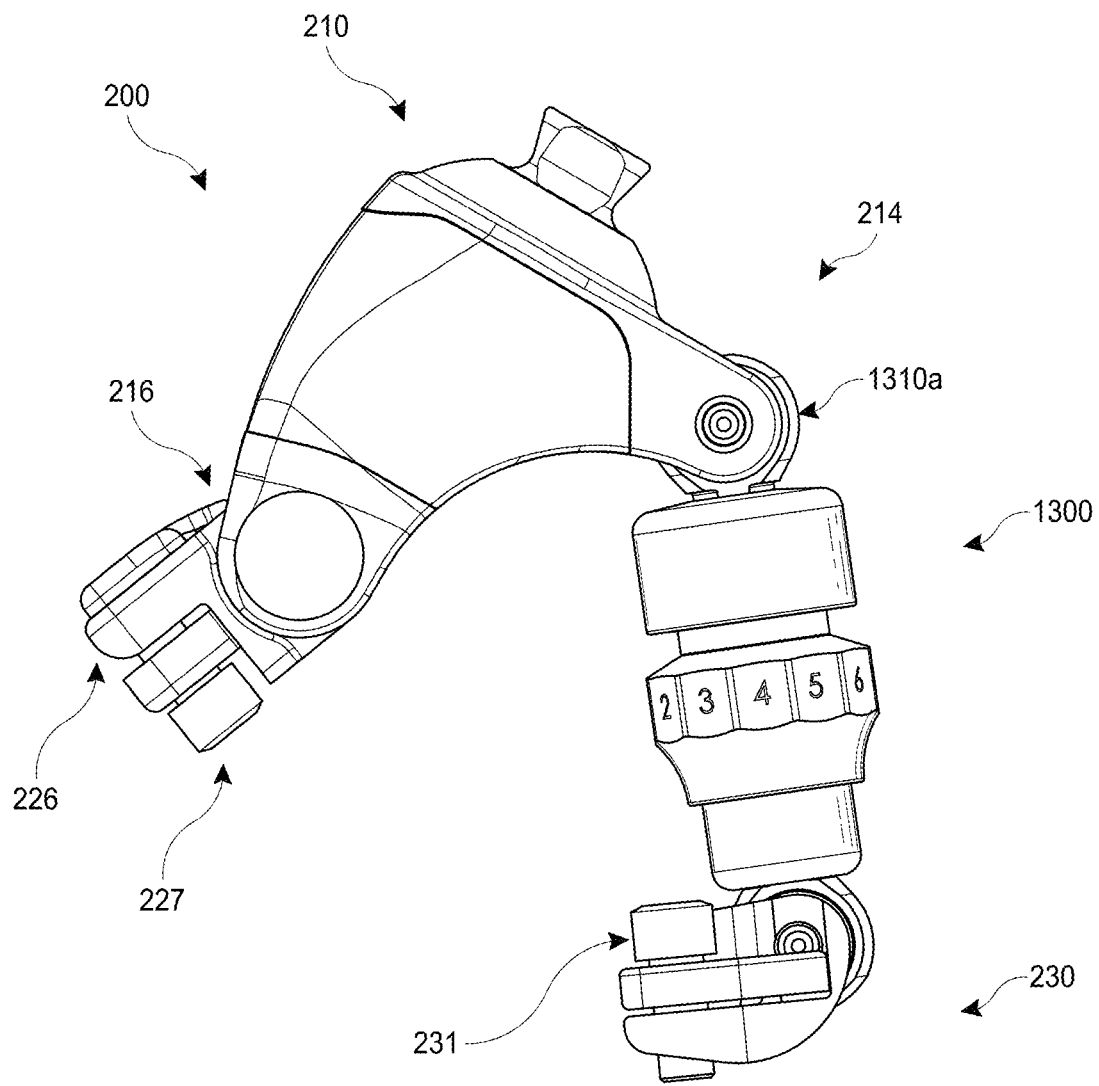
FIG. 21 illustrates the actuator of FIGS. 11-20B incorporated into an example embodiment of an ankle module.
Figure 22B:
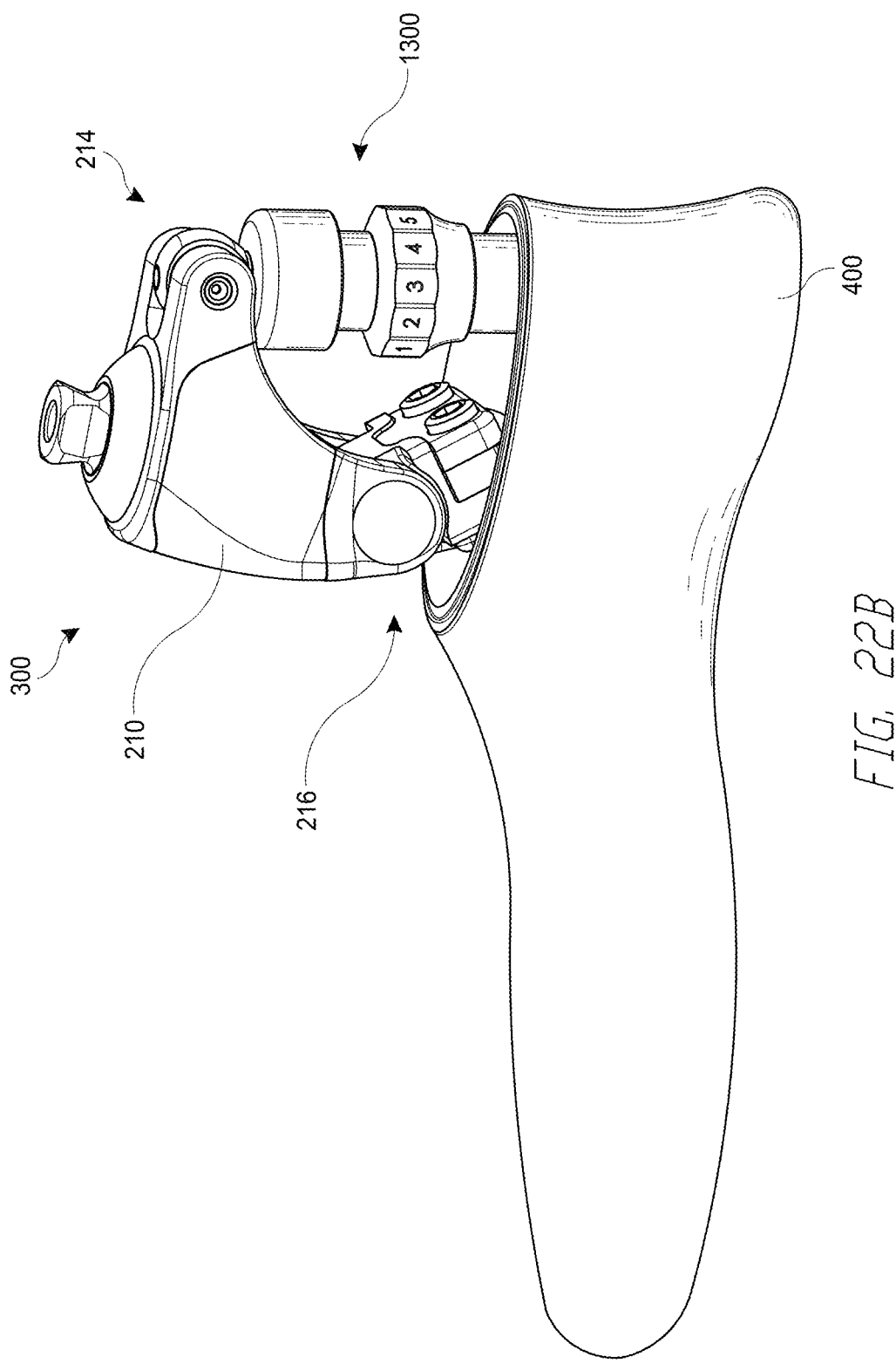

In some embodiments, the actuator 100, 1300 can be used in a prosthetic joint. For example, a prosthetic ankle incorporating the actuator 1300 is shown in the example embodiments of FIGS. 21-22B. As shown, a prosthetic ankle module 200 incorporating the actuator 1300 can include an upper attachment portion 210 and a lower attachment portion 230. The upper connector 1310, e.g., the ball joint 1310a of the upper connector 1310, is coupled to the upper attachment portion 210, and the lower connector 1312, e.g., the ball joint 1312a of the lower connector 1312, is coupled to the lower attachment portion 230. The upper connector 1310 has the ball joint 110a at one end of the upper connector 1310 and the threaded shaft 111 extending between the ball joint 1310a and a distal end 1310b at an opposite end of the upper connector 1310. The lower connector 1312 has a ball joint 112a at one end of the lower connector 1312 and a threaded shaft 113 (shown in FIG. 20)

extending between the ball joint 1312a and a proximal end 1312b at an opposite end of the lower connector 1312. The inner shaft 1334 includes an upper internally threaded portion 1335a and a lower internally threaded portion 1335b to threadedly engage the threaded shafts 1311, 1313 of the upper connector 1310 and the lower connector 1312, respectively. FIG. 22A illustrates an example embodiment of a prosthetic foot 300 incorporating the ankle module 200. FIG. 22B illustrates another example embodiment of a prosthetic foot 300 incorporating the ankle module 200 and disposed in a cosmesis 400. The actuator 100 can be incorporated in the ankle module 200 and/or the prosthetic foot 300 in the same or a similar manner as the actuator 1300. Additional examples of incorporating an actuator into a prosthetic foot for heel height adjustment purposes are illustrated in U.S. patent application Ser. No. 14/704,117, filed May 5, 2015 and entitled "PROSTHETIC FOOT WITH REMOVABLE FLEXIBLE MEMBERS," the entirety of which is incorporated herein by reference and should be considered a part of this specification.

In the illustrated embodiment, the prosthetic foot 300 includes an upper foot member 240, an intermediate foot member 250, and a lower foot member 260. In the illustrated embodiment, the lower foot member 260 extends from a heel end to a toe end, the upper foot member 240 is L-shaped, the intermediate foot member 250 is generally straight, and the intermediate 250 and upper 240 foot members extend from proximal ends to distal ends that are proximal of the toe end of the lower foot member 260. However, other numbers and configurations of foot members are also possible, and the ankle module 200 can be adapted for use with other arrangements of foot members. For example, the upper foot member 240 can be C-shaped. The lower foot member 260 may not extend to a toe end, and the upper 240 or intermediate 250 foot member may instead extend to a toe end. In some embodiments, the prosthetic foot 300 may only include an upper foot member 240 and a lower foot member 260.

In the illustrated embodiments, the upper attachment portion 210 has three connection portions or points 212, 214, 216. The first connection portion 212 attaches the ankle module 200 to a user or another prosthetic device. In the illustrated embodiment, the first connection portion is a pyramid connector, although other connectors and adapters are also possible. The upper connector ball joint 1310a connects to the upper attachment portion 210 at the second connection point 214 rotatably or non-rotatably. The upper attachment portion 210 connects to the proximal end of the upper foot member 240 at the third connection portion 216. In the illustrated embodiment, a brace 226 is attached, pivotably or non-pivotably, to the upper attachment portion 210 at the third connection portion 216, and the upper foot member 240 is coupled to the brace 226. The upper foot member 240 can be secured to the brace 226 via one or more fasteners 227, such as one or more screws. In an embodiment in which the prosthetic foot 300 only includes an upper foot member 240 and a lower foot member 260, the ankle module 200 can be modified such that the third 216 connection portion couples to the upper foot member 240. In the illustrated embodiment, the third connection portion 216 is in a front portion of the upper attachment portion 210, and the second connection portion 214 is in a rear portion of the upper attachment portion 210. Therefore, the actuator 1300 is located at a rear portion of the ankle module 200. However, in other embodiments the actuator 1300 can be positioned in a front portion of the ankle module 200.

In the illustrated embodiment, the lower attachment portion 230 couples to the proximal end of the intermediate foot member 250. The intermediate foot member 250 can be secured to the lower attachment portion 230 via one or more fasteners 231, such as one or more screws. The lower attachment portion also couples to the lower connector 1312, either rotatably or non-rotatably, at a fourth connection portion 232.

The ankle module 200 can advantageously provide a passive prosthetic ankle with ankle motion that is closer to a biological ankle than previously available passive prosthetic feet. The prosthetic foot 300 can advantageously store energy with less effort for the user, which can help avoid excessive pressure on the user's residual limb, while still returning high energy during the push-off or toe-off phase of the gait cycle. The fourth connection portion 232, which can be a pivot point, can act as an ankle joint and create a fixed pivot axis for ankle motion during use. This allows for separate stiffness profiles to be achieved for ankle motion at different locations in stance phase. For example, in mid-stance, ankle stiffness is low, which helps reduce moment and pressure on the user's residual limb. During initial loading of the foot 300 during gait, the stiffness is lower than previously available prosthetic feet. This reduced stiffness allows for lower resistance to initial dorsiflexion as the foot 300 moves through stance and less moment required from the residual limb to load the foot 300. As the user moves through stance, the prosthetic foot 300 progressively stiffens. For a given load, the prosthetic foot 300 has higher displacement and a greater range of ankle motion than previously available prosthetic feet. The prosthetic foot 300 also stores energy over a longer period of times than previously available prosthetic feet and therefore returns more energy during push-off.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot having an adjustable heel height, the prosthetic foot comprising:
    a first plate extending between an anterior end and a posterior end;
    a second plate disposed below the first plate and extending between an anterior end and a posterior end, the first and second plates coupled at the anterior end of the second plate, the posterior end of the second plate extending rearward of the posterior end of the first plate;
    an adapter comprising a first joint and a second joint, the first joint pivotally coupled to the posterior end of the first plate; and
    a non-powered heel height adjustment module, comprising:
        a first component coupled to the second joint of the adapter at a proximal connector joint of the first component;
        a second component coupled to the posterior end of the second plate at a distal connector joint of the second component; and
        a third component configured to engage the first and second components from opposite ends of the third component, wherein the third component is configured to be manually translated relative to a longitudinal axis of one or both of the first or second components to adjust the heel height of the prosthetic foot, a position of the third component relative to the first and second components configured to be reversibly locked by magnets.

2. The prosthetic foot of claim 1, wherein the magnets comprise at least one magnet coupled to the first component and at least one magnet coupled to the third component.

3. The prosthetic foot of claim 2, wherein the at least one magnet coupled to the first component extends circumferentially around the longitudinal axis of the first component.

4. The prosthetic foot of claim 2, wherein the first component comprises a housing, the at least one magnet coupled to the first component being secured within the housing.

5. The prosthetic foot of claim 4, wherein the at least one magnet coupled to the first component is secured about a longitudinal axis of the housing.

6. The prosthetic foot of claim 4, wherein a proximal portion of the third component partially extends into an opening of the housing.

7. The prosthetic foot of claim 2, wherein the at least one magnet coupled to the third component extends circumferentially around a longitudinal axis of the third component.

8. The prosthetic foot of claim 2, wherein a proximal portion of the third component is configured to threadedly engage the first component and a distal portion of the third component is configured to threadedly engage the second component.

9. The prosthetic foot of claim 2, wherein one or both of the at least one magnet coupled to the first component and the at least one magnet coupled to the third component are cylindrical.

10. The prosthetic foot of claim 2, wherein one or both of the at least one magnet coupled to the first component and the at least one magnet coupled to the third component comprise split polarities or adjacent sections of alternating polarities.

11. The prosthetic foot of claim 1, further comprising a third foot plate located below the second foot plate, an anterior end of the third foot plate defining a toe end of the prosthetic foot, and a posterior end of the third foot plate defining a heel end of the prosthetic foot.

12. The prosthetic foot of claim 11, wherein the third foot plate is coupled to the anterior ends of the first and second foot plates, the anterior ends of the first and second foot plates being more posterior than the anterior end of the third foot plate.

13. The prosthetic foot of claim 1, wherein the third component is configured to be manually translated relative to the longitudinal axis of one or both of the first or second components by a manual force on the third component to adjust the heel height.

14. An actuator of a prosthetic foot, the actuator having an adjustable length and comprising:
a first component comprising a proximal connector joint;
a second component comprising a distal connector joint; and
a third component configured to engage the first and second components from opposite ends of the third component, wherein the third component is configured to be manually translated relative to a longitudinal axis of one or both of the first or second components to adjust a length of the actuator, a position of the third component relative to the first and second components configured to be reversibly locked by magnets,
wherein the actuator is non-powered.

15. The actuator of claim 14, wherein the first component comprises a housing and the magnets comprises at least one magnet secured within the housing about a longitudinal axis of the housing.

16. The actuator of claim 15, wherein a proximal portion of the third component partially extends into an opening of the housing and is configured to threadedly engage a threaded shaft extending through the housing, a distal portion of the third component is configured to threadedly engage the second component.

17. The actuator of claim 15, wherein the magnets further comprise at least one magnet coupled to the third component and extending circumferentially around a longitudinal axis of the third component.

18. The actuator of claim 17, wherein one or both of the at least one magnet coupled to the first component and the at least one magnet coupled to the third component are cylindrical.

19. The actuator of claim 17, wherein one or both of the at least one magnet coupled to the first component and the at least one magnet coupled to the third component comprise split polarities or adjacent sections of alternating polarities.

20. An ankle module of a prosthetic foot, comprising:
a proximal attachment portion;
a distal attachment portion; and
the actuator of claim 14.

21. The ankle module of claim 20:
wherein the proximal attachment portion includes a first connection portion, a second connection portion, and a third connection portion, the first connection portion comprising an adapter configured to couple the ankle module to a user or to another prosthetic device, the second connection portion configured to connect to the proximal connector joint of the first component of the actuator, and the third connection portion configured to connect to a foot member of a prosthetic foot; and
wherein the distal attachment portion includes a fourth connection portion, the fourth connection portion configured to couple to a second foot member of the prosthetic foot.

* * * * *